US012745722B2

(12) United States Patent
De Lange et al.

(10) Patent No.: US 12,745,722 B2
(45) Date of Patent: Sep. 29, 2026

(54) ***Bremia lactucae* RESISTANCE SG01**

(71) Applicant: Syngenta Crop Protection AG, Basel (CH)

(72) Inventors: Michel De Lange, Enkhuizen (NL); Anoma Akuvi Lokossou, Enkhuizen (NL)

(73) Assignee: SYNGENTA CROP PROTECTION AG, Basel (CH)

( * ) Notice: Subject to any disclaimer, the term of this patent is extended or adjusted under 35 U.S.C. 154(b) by 643 days.

(21) Appl. No.: 18/001,949

(22) PCT Filed: Jul. 5, 2021

(86) PCT No.: PCT/EP2021/068479
§ 371 (c)(1),
(2) Date: Dec. 15, 2022

(87) PCT Pub. No.: WO2022/008422
PCT Pub. Date: Jan. 13, 2022

(65) Prior Publication Data

US 2023/0301259 A1 Sep. 28, 2023

(30) Foreign Application Priority Data

Jul. 6, 2020 (EP) .................................... 20184325

(51) Int. Cl.
*A01H 6/14* (2018.01)
*A01H 1/04* (2006.01)
*A01H 5/12* (2018.01)

(52) U.S. Cl.
CPC ........... *A01H 6/1472* (2018.05); *A01H 1/045* (2021.01); *A01H 5/12* (2013.01)

(58) Field of Classification Search
None
See application file for complete search history.

(56) References Cited

U.S. PATENT DOCUMENTS

| | | | | |
|---|---|---|---|---|
| 6,350,933 | B1 * | 2/2002 | Michelmore | C12N 15/8279 435/6.12 |
| 2004/0226060 | A1 | 11/2004 | Lambalk et al. | |
| 2012/0117683 | A1 | 5/2012 | Zonneveld et al. | |
| 2013/0269066 | A1 | 10/2013 | Thabuis et al. | |
| 2016/0007552 | A1 | 1/2016 | Scheurwater | |
| 2016/0374303 | A1 | 12/2016 | Jeuken et al. | |
| 2017/0064918 | A1 | 3/2017 | Brugmans et al. | |
| 2020/0029523 | A1 * | 1/2020 | Scheurwater | A01H 1/045 |

FOREIGN PATENT DOCUMENTS

| | | | |
|---|---|---|---|
| CN | 101098965 | A | 1/2008 |
| JP | 2010519923 | A | 6/2010 |
| JP | 2012531920 | A | 12/2012 |
| WO | 2011/003783 | A1 | 1/2011 |
| WO | 2014/131857 | A1 | 9/2014 |

OTHER PUBLICATIONS

Kuang et al. Plant Cell. 16:2870-2894. (Year: 2004).*
Genbank Accession AY193575 (Year: 2016).*
USDA, "Applying for a Plant Variety Certificate of Protection", https://www.ams.usda.gov/services/pvpo/application-help/apply, accessed May 1, 2023.*
UPOV, 2017, Explanatory Notes on Essentially Derived Varieties Under the 1991 Act of the UPOV Convention.*
Ex Parte C (USPQ 2d 1492 (1992).*
Ex Parte McGowen—Board Decision in U.S. Appl. No. 14/996,093. (Year: 2020).*
Huan et al. Plant Physiology. 155:645-655. (Year: 2011).*
Großinsky et al. Journal of Experimental Botany. 66(18):5429-5440. (Year: 2015).*
Third Party Observation for application No. EP20210735738 dated Oct. 12, 2023.
Third Party Observation in Australian Patent No. 2021303718 in the name of Syngenta Crop Protection AG filed by Bejo Zaden B.V. on Feb. 15, 2024.
Reyes-Chin-WO S., "Genome assembly with in vitro proximity ligation data and whole genome triplication in lettuce", Nature Communications, vol. 8, 2017, 14953.
ISR for PCT/EP2021/068479. Date of search Sep. 14, 2021.
Lebeda et al—Wild *Lactuca* species, their genetic diversity, resistance to diseases and pests, and exploitation in lettuce breeding—European Journal of Plant Pathology (2014)—vol. 138 No. 3—Aug. 2, 2013—pp. 597-640.
Subsidies for Examination submitted by Bejo Zaden with respect to Brazilian Patent Application No. BR112023000244-3 with Annexes I, II and III, dated Dec. 17, 2024, 33 Pages. (with English translation).
Subsidies for Examination submitted by Bejo Zaden with respect to Brazilian Patent Application No. BR112023000244-3 with Annexes I, II and III, dated Nov. 26, 2024, 32 Pages. (with English translation).
Beharav A., et al., "Resistance in Natural Populations of Three Wild *Lactuca* Species From Israel to Highly Virulent Californian Isolates of *Bremia lactucae*," Genetical Resource Crop Evolution, 2013, vol. 61, No. 3, pp. 603-609.
International Preliminary Report on Patentability for International Application No. PCT/EP2021/068479, mailed Jan. 19, 2023, 8 Pages.

(Continued)

*Primary Examiner* — David R Byrnes
(74) *Attorney, Agent, or Firm* — Karen A. Magri

(57) ABSTRACT

The present invention relates to novel lettuce plants displaying resistance to *Bremia lactucae*. The present invention also relates to seeds and parts of said plants, for example leaves and heads. The present invention further relates to methods of making and using such seeds and plants. The present invention also relates to novel genetic sequences associated with said resistance to *Bremia lactucae* and to molecular markers associated with said novel genetic sequences.

11 Claims, No Drawings

Specification includes a Sequence Listing.

(56) References Cited

OTHER PUBLICATIONS

Ling L., et al., "Genetic Comparisons between *Lactuca pulchella* (Pursh) DC and its Closely Related Lettuce Species," Fujian Journal of Agricultural Sciences, 2017, vol. 32, No. 10, pp. 1077-1081.
Bejo Iberica, S.L.U., "Informacion Variedades Cultivos de Hoja 2018-2019," p. 8, Feb. 20, 2019 (https://issuu.com/bejozaden/docs/bejo-catalogocultivosdehojaespana18).†
Bejo Grains France sarl, "Salades et Jeunes Pousses 2018-2019," p. 4, Jan. 22, 2018 (https://issuu.com/bejozaden/docs/bejo-brochure_salade_v6_lr).†
Bejo Samen GmbH, "Salat Sorteninfo 2019-2020," p. 7, Nov. 26, 2019 (https://issuu.com/bejozaden/docs/salat_de_2019-2020_lr).†

* cited by examiner
† cited by third party

SEQUENCE LISTING

<160> NUMBER OF SEQ ID NOS: 20

<210> SEQ ID NO 1
<211> LENGTH: 155
<212> TYPE: DNA
<213> ORGANISM: Lactuca sativa
<220> FEATURE:
<221> NAME/KEY: misc_feature
<222> LOCATION: (2)..(2)
<223> OTHER INFORMATION: n is A, T, C, or G
<220> FEATURE:
<221> NAME/KEY: misc_feature
<222> LOCATION: (51)..(51)
<223> OTHER INFORMATION: n is A, T, C, or G
<220> FEATURE:
<221> NAME/KEY: misc_feature
<222> LOCATION: (90)..(90)
<223> OTHER INFORMATION: n is A, T, C, or G
<220> FEATURE:
<221> NAME/KEY: misc_feature
<222> LOCATION: (101)..(101)
<223> OTHER INFORMATION: n is A, T, C, or G
<220> FEATURE:
<221> NAME/KEY: misc_feature
<222> LOCATION: (112)..(112)

```
<223> OTHER INFORMATION: r is A or G

<400> SEQUENCE: 1

tntaaagatt agatacaggg cagggaggaa tgcctttgag ataaatgagg ngatcgacag     60

tgtcatgaga cgatacaaag agatcaaccn ggcagatcat ncaattcctc crggaagggt    120

tgattccatg aagccatcca catcaacacc atcag                               155


<210> SEQ ID NO 2
<211> LENGTH: 22
<212> TYPE: DNA
<213> ORGANISM: Artificial Sequence
<220> FEATURE:
<223> OTHER INFORMATION: synthesized

<400> SEQUENCE: 2

agatacaggg cagggaggaa tg                                              22


<210> SEQ ID NO 3
<211> LENGTH: 15
<212> TYPE: DNA
<213> ORGANISM: Artificial Sequence
<220> FEATURE:
<223> OTHER INFORMATION: synthesized

<400> SEQUENCE: 3

acccttcccg gagga                                                      15


<210> SEQ ID NO 4
<211> LENGTH: 16
<212> TYPE: DNA
<213> ORGANISM: Artificial Sequence
<220> FEATURE:
<223> OTHER INFORMATION: synthesized

<400> SEQUENCE: 4

caacccttcc tggagg                                                     16


<210> SEQ ID NO 5
<211> LENGTH: 23
<212> TYPE: DNA
<213> ORGANISM: Artificial Sequence
<220> FEATURE:
<223> OTHER INFORMATION: synthesized

<400> SEQUENCE: 5

tgatgtggat ggcttcatgg aat                                             23


<210> SEQ ID NO 6
<211> LENGTH: 157
<212> TYPE: DNA
<213> ORGANISM: Lactuca sativa
<220> FEATURE:
<221> NAME/KEY: misc_feature
<222> LOCATION: (101)..(101)
<223> OTHER INFORMATION: n is A, T, C, or G
<220> FEATURE:
<221> NAME/KEY: misc_feature
<222> LOCATION: (104)..(104)
<223> OTHER INFORMATION: n is A, T, C, or G
<220> FEATURE:
<221> NAME/KEY: misc_feature
<222> LOCATION: (112)..(112)
<223> OTHER INFORMATION: r is A or G

<400> SEQUENCE: 6

ggtacacgct cgcagtgaaa gccttggaga taactcagga gatcgatcat gccatgaaac     60
```

aactctctca gatagaatgg actgatgatt cagttccttt nggnagaaat grttccacaa 120
aggcatccac ctctacacca tcaagtgatt acaatga 157

<210> SEQ ID NO 7
<211> LENGTH: 21
<212> TYPE: DNA
<213> ORGANISM: Artificial Sequence
<220> FEATURE:
<223> OTHER INFORMATION: synthesized

<400> SEQUENCE: 7
cgcagtgaaa gccttggaga t 21

<210> SEQ ID NO 8
<211> LENGTH: 19
<212> TYPE: DNA
<213> ORGANISM: Artificial Sequence
<220> FEATURE:
<223> OTHER INFORMATION: synthesized

<400> SEQUENCE: 8
tgcctttgtg gaatcattt 19

<210> SEQ ID NO 9
<211> LENGTH: 18
<212> TYPE: DNA
<213> ORGANISM: Artificial Sequence
<220> FEATURE:
<223> OTHER INFORMATION: synthesized

<400> SEQUENCE: 9
cctttgtgga accatttc 18

<210> SEQ ID NO 10
<211> LENGTH: 22
<212> TYPE: DNA
<213> ORGANISM: Artificial Sequence
<220> FEATURE:
<223> OTHER INFORMATION: synthesized

<400> SEQUENCE: 10
cacttgatgg tgtagaggtg ga 22

<210> SEQ ID NO 11
<211> LENGTH: 138
<212> TYPE: DNA
<213> ORGANISM: Lactuca sativa
<220> FEATURE:
<221> NAME/KEY: misc_feature
<222> LOCATION: (41)..(41)
<223> OTHER INFORMATION: n is A, T, C, or G
<220> FEATURE:
<221> NAME/KEY: misc_feature
<222> LOCATION: (62)..(62)
<223> OTHER INFORMATION: n is A, T, C, or G
<220> FEATURE:
<221> NAME/KEY: misc_feature
<222> LOCATION: (99)..(99)
<223> OTHER INFORMATION: r is A or G

<400> SEQUENCE: 11
gcacttgcaa gcatgagaca gctcgaagag ttaactataa natattgcaa ggccttgaaa 60
gngattgtga agaaggaaga agacaatgca tcatcatcnt catcgaagga ggttgtggtc 120
ttgcctcatc taaagtcc 138

<210> SEQ ID NO 12
<211> LENGTH: 21
<212> TYPE: DNA
<213> ORGANISM: Artificial Sequence
<220> FEATURE:
<223> OTHER INFORMATION: synthesized

<400> SEQUENCE: 12
gcatgagaca gctcgaagag t 21

<210> SEQ ID NO 13
<211> LENGTH: 18
<212> TYPE: DNA
<213> ORGANISM: Artificial Sequence
<220> FEATURE:
<223> OTHER INFORMATION: synthesized

<400> SEQUENCE: 13
ccttcgatga cgatgatg 18

<210> SEQ ID NO 14
<211> LENGTH: 19
<212> TYPE: DNA
<213> ORGANISM: Artificial Sequence
<220> FEATURE:
<223> OTHER INFORMATION: synthesized

<400> SEQUENCE: 14
tccttcgatg atgatgatg 19

<210> SEQ ID NO 15
<211> LENGTH: 18
<212> TYPE: DNA
<213> ORGANISM: Artificial Sequence
<220> FEATURE:
<223> OTHER INFORMATION: synthesized

<400> SEQUENCE: 15
tgaggcaaga ccacaacc 18

<210> SEQ ID NO 16
<211> LENGTH: 80
<212> TYPE: DNA
<213> ORGANISM: Lactuca sativa
<220> FEATURE:
<221> NAME/KEY: misc_feature
<222> LOCATION: (6)..(6)
<223> OTHER INFORMATION: n is A, T, C, or G
<220> FEATURE:
<221> NAME/KEY: misc_feature
<222> LOCATION: (6)..(6)
<223> OTHER INFORMATION: m is A or C
<220> FEATURE:
<221> NAME/KEY: misc_feature
<222> LOCATION: (41)..(41)
<223> OTHER INFORMATION: n is a, c, g, or t

<400> SEQUENCE: 16
agacgnttta acgacctggc ccaacattcc atgaaccacc ngactggttt tgggcaattt 60
agtcgggtac ctgcctttgc 80

<210> SEQ ID NO 17
<211> LENGTH: 20
<212> TYPE: DNA
<213> ORGANISM: Artificial Sequence
<220> FEATURE:
<223> OTHER INFORMATION: synthesized

```
<400> SEQUENCE: 17

acgacctggc ccaacattcc                                                20


<210> SEQ ID NO 18
<211> LENGTH: 15
<212> TYPE: DNA
<213> ORGANISM: Artificial Sequence
<220> FEATURE:
<223> OTHER INFORMATION: synthesized

<400> SEQUENCE: 18

tgaaccaccc gactg                                                     15


<210> SEQ ID NO 19
<211> LENGTH: 16
<212> TYPE: DNA
<213> ORGANISM: Artificial Sequence
<220> FEATURE:
<223> OTHER INFORMATION: synthesized

<400> SEQUENCE: 19

tgaaccacca gactgg                                                    16


<210> SEQ ID NO 20
<211> LENGTH: 22
<212> TYPE: DNA
<213> ORGANISM: Artificial Sequence
<220> FEATURE:
<223> OTHER INFORMATION: synthesized

<400> SEQUENCE: 20

gtacccgact aaattgccca aa                                             22
```

*Bremia lactucae* RESISTANCE SG01

RELATED APPLICATION INFORMATION

This application is a national stage entry under 35 U.S.C. § 371 of International Application No. PCT/EP2021/068479, filed 5 Jul. 2021, which claims the benefit of European Application No. 20184325.7, filed 6 Jul. 2020, the contents of which are incorporated herein by reference in their entireties.

STATEMENT REGARDING ELECTRONIC SUBMISSION OF A SEQUENCE LISTING

A Sequence Listing in ASCII text format, submitted under 37 C.F.R. § 1.821, entitled "SEQLTXT-1.txt", 4,778 bytes in size, generated on Jul. 6, 2020 and filed via EFS-Web is provided in lieu of a paper copy. This Sequence Listing is hereby incorporated by reference into the specification for its disclosures.

FIELD OF THE INVENTION

The present invention relates to novel lettuce plants displaying resistance to *Bremia lactucae*. The present invention also relates to seeds and parts of said plants, for example leaves and heads. The present invention further relates to methods of making and using such seeds and plants. The present invention also relates to novel genetic sequences associated with said resistance to *Bremia lactucae* and to molecular markers associated with said novel genetic sequences.

BACKGROUND OF THE INVENTION

Plant pathogens are known to cause massive damage to important crops, resulting in significant agricultural losses with widespread consequences for both the food supply and other industries that rely on plant materials. As such, there is a long felt need to reduce the incidence and/or impact of agricultural pests on crop production.

An example of such a pathogen is the fungus *Bremia lactucae*, which causes downy mildew. *B. lactucae* occurs worldwide and represents a great problem for both the yield and quality of cultivated lettuce (*Lactuca sativa*). The fungus can infect the lettuce plant at any stage of growth, after which the first symptoms of downy mildew become visible as chlorotic yellow spots on the leaf surface. Within 24-48 hours a white fluffy fungus growth becomes visible on the lower leaf surface as an indication of spore formation. During the infection the lesion spots become increasingly larger and more chlorotic until the leaves become completely brown.

*Bremia lactucae* belongs to the group Oomycetes, a class of relatively primitive fungi. Other members of this group are, for instance, *Pythium* and *Phytophthora*. *B. lactucae* contains different physiological species ("physios"), is a very variable pathogen, and is host-specific. New physios occur relatively frequently through mutation of the avirulence genes during spore formation preceding the propagation of *B. lactucae*.

Within the genus *Lactucae*, to which the cultivated lettuce *L. sativa* belongs, there are a number of known resistances to *B. lactucae*. These resistances are generally race-specific and based on qualitative genes, known as Dm (downy mildew)-resistance genes. The resistance mechanism is known as a gene-for-gene mechanism based on the specific interaction between products of the Dm-resistance gene and the pathogen-specific avirulence gene (HR reaction), which results in resistance of the lettuce plant.

Due to the high variability of *B. lactucae* and the frequent emergence of new physios, the race-specific resistance mediated by the various Dm resistance genes can be rapidly broken by newly emerging physios of the *Bremia* pathogen.

There remains a need for novel resistances against the fungal pathogen *Bremia lactucae*, in particular. broad spectrum resistance against this fungal pathogen.

SUMMARY OF THE INVENTION

The present invention addresses the need for additional and improved resistances to *Bremia lactucae* by providing novel lettuce plants, and parts and seeds thereof, comprising a *Bremia* resistance trait designated as "SG01". Also provided are nucleic acid markers for identifying and producing lettuce plants (e.g., *L. sativa* plants), and parts and seeds thereof, comprising the *Bremia* resistance trait. In particular embodiments, the invention discloses a novel source of resistance to *Bremia*: CGN23091, a wild *Lactuca serriola* accession. By introgressing the *Bremia* resistance conferring sequences from the wild source into cultivated lettuce plants (e.g., *L. sativa*), a qualitative *Bremia* resistance was conferred to the cultivated lettuce plant. The *Bremia* resistance-conferring introgressed sequence, located on chromosome 2, is of a dominant nature; hence one copy of the sequence provides a *Bremia* resistance phenotype.

Altogether, the characteristics of the *Bremia* resistant lettuce plant disclosed within the present invention provide a lettuce grower with novel solutions to enhance economic and commercial efficiency when deploying lettuce varieties in a *Bremia* pressured field. Further, as well understood by those skilled in the art, new *Bremia* resistances can be stacked with other *Bremia* resistances in a single plant and can provide an improved spectrum of resistance against multiple races/isolates, protection against newly emerging races/isolates, and can delay a breakdown in existing *Bremia* resistances.

In a first embodiment, the invention provides a lettuce plant (e.g., a cultivated lettuce plant, such as a *Lactuca sativa* plant) resistant to *Bremia lactucae* comprising an introgressed sequence from *Lactuca serriola* that confers a qualitative and dominant resistance to *Bremia lactucae*, wherein said introgressed sequence is comprised in *Lactuca serriola* accession CGN23091 or in *Lactuca sativa* line 18LEN002364, and wherein said introgressed sequence is located on chromosome 2 and comprises one or more of the following SNP markers:

a) a G genotype in the heterozygous or homozygous state for SNP marker SL1831 in SEQ ID NO: 1;
b) an A genotype in the heterozygous or homozygous state for SNP marker SL1847 in SEQ ID NO: 6;
c) a G genotype in the heterozygous or homozygous state for SNP marker SL1887 in SEQ ID NO: 11; and/or
d) a C genotype in the heterozygous or homozygous state for SNP marker SL1883 in SEQ ID NO: 16.

In a further embodiment, the invention provides a lettuce plant (e.g., a cultivated lettuce plant, such as a *Lactuca sativa* plant) with enhanced resistance to *Bremia lactucae* comprising an introgressed sequence from *Lactuca serriola* that confers a qualitative and dominant resistance to *Bremia lactucae*, wherein said introgressed sequence is comprised in *Lactuca serriola* accession CGN23091 or in *Lactuca sativa* line 18LEN002364, and wherein said introgressed sequence is located on chromosome 2 and comprises one or more of the following SNP markers:

a) a G genotype in the heterozygous or homozygous state for SNP marker SL1831 in SEQ ID NO: 1;

b) an A genotype in the heterozygous or homozygous state for SNP marker SL1847 in SEQ ID NO: 6;

c) a G genotype in the heterozygous or homozygous state for SNP marker SL1887 in SEQ ID NO: 11; and/or d) a C genotype in the heterozygous or homozygous state for SNP marker SL1883 in SEQ ID NO: 16;

wherein the resistance of said lettuce plant to *B. lactucae* is enhanced as compared with a control lettuce plant (e.g., a *L. sativa* plant) not comprising said introgressed sequence.

In representative embodiments:

a) the G genotype for marker SL1831 can be identified in a PCR by amplification of a nucleic acid fragment with a pair of oligonucleotide primers: forward primer of SEQ ID NO: 2 and reverse primer of SEQ ID NO: 5, and probe of SEQ ID NO: 3;

b) the A genotype for SNP marker SL1847 can be identified in a PCR by amplification of a nucleic acid fragment with a pair of oligonucleotide primers: forward primer of SEQ ID NO: 7 and reverse primer of SEQ ID NO: 10, and probe of SEQ ID NO: 8;

c) the G genotype for SNP marker SL1887 can be identified in a PCR by amplification of a nucleic acid fragment with a pair of oligonucleotide primers: forward primer of SEQ ID NO: 12 and reverse primer of SEQ ID NO: 15, and probe of SEQ ID NO: 13; and d) the C genotype for SNP marker SL1883 can be identified in a PCR by amplification of a nucleic acid fragment with a pair of oligonucleotide primers: forward primer of SEQ ID NO: 17 and reverse primer of SEQ ID NO: 20, and probe of SEQ ID NO: 18.

In embodiments, the plant according to the invention is a cultivated plant.

In embodiments, the introgressed sequence of the invention comprises one or more of SEQ ID NO: 1 having a resistance marker allele represented by nucleotide G at position 112, SEQ ID NO: 6 having a resistance marker allele represented by nucleotide A at position 112, SEQ ID NO: 11 having a resistance marker allele represented by nucleotide G at position 99 and/or SEQ ID NO: 16 having a resistance marker allele represented by nucleotide C at position 41, or a sequence that is at least 80%, 85%, 90%, 95%, 96%, 97%, 98%, 99% or more identical to one or more of the foregoing sequences and comprises the resistance marker allele.

In embodiments, the plant according to the invention is heterozygous for the one or more SNP markers (e.g., is heterozygous for the introgressed sequence and the SG01 *Bremia* resistance).

In embodiments, the plant according to the invention is homozygous (for the one or more SNP markers (e.g., is homozygous for the introgressed sequence and the SG01 *Bremia* resistance).

In embodiments, the plant according to the invention comprises two or more, three or more or all four of SNP markers SL1831, SL1847, SLI1887 and/or SLI1883 (each in heterozygous or homozygous form).

In representative embodiments, the plant according to the present invention comprises at least the following SNP markers (either or both markers in heterozygous or homozygous form):

SSIL1831 and SL1847;
SSIL1831 and SL1883;
SSIL1831 and SL1887;
SSIL1847 and SLI1883;
SIL1847 and SL1887; or
SSIL1883 and SLI1887.

For example, markers SL1883 and SL1887 can be used together, optionally with the addition of other markers. As another exemplary illustration, markers SL1847 and SLI1887 can be used in combination, optionally with the addition of other markers.

In embodiments, the introgressed sequence of the invention confers resistance at least against *Bremia lactucae* races BI 16-36EU.

In embodiments, the plant according to the present invention is obtained by crossing *Lactuca serriola* accession CGN23091 or lettuce 18LEN002364 with a second lettuce plant that does not comprise said introgressed sequence conferring resistance to *Bremia lactucae* (e.g., does not comprise the SG01 *Bremia* resistance).

In embodiments, the plant according to the invention is an inbred, a dihaploid or a hybrid plant. Generally, the plants of the invention are diploid.

As a further aspect, the invention provides a plant of *Lactuca sativa* line 18LEN002364.

It is a further embodiment to provide a plant part, organ or tissue obtained from a lettuce plant according to any of the embodiments described herein, including but not limited to heads, leaves, cores, stems, roots, flowers or flower parts, shoots, gametophytes, sporophytes, pollen, anthers, microspores, egg cells, zygotes, embryos, meristematic regions, callus tissue, seeds, cuttings, cell or tissue cultures or any other part or product of the plant, which comprise the introgressed sequence. In embodiments, the plant part, organ or tissue exhibits the *Bremia* resistance according to the invention, particularly when grown into a lettuce plant that produces lettuce leaves and/or heads.

Further provided is a seed that produces a plant according to the invention.

Still further is provided a seed produced by a plant according to the invention.

In another embodiment is considered the use of a lettuce plant, plant part or seed according to any of the embodiments of the invention for producing and harvesting a lettuce head and/or leaves.

In another embodiment, the invention relates to the use of a lettuce plant, plant part (e.g., head or leaves) or seed according to any embodiment described herein, to produce a further lettuce plant, plant part or seed having the *Bremia* resistance of the invention.

In another embodiment the invention relates to the use of a lettuce plant, plant part or seed according to any embodiment of the invention, wherein the lettuce plant, plant part or seed is *L. sativa* 18LEN002364, or a progeny or an ancestor thereof.

In still a further embodiment the invention relates to the use of a lettuce plant, plant part or seed according to any embodiment of the invention, wherein the lettuce plant, plant part or seed is *L. serriola* accession CGN23091, or a progeny or an ancestor thereof.

As another embodiment, the invention provides a method for producing a lettuce plant with enhanced resistance resistant to *Bremia lactucae* (e.g., as compared with a control plant), the method comprising:

a) crossing a lettuce plant according to the present invention with a second lettuce plant lacking said introgressed sequence conferring resistance to *Bremia lactucae* to produce progeny plants;

b) selecting a progeny plant comprising said introgressed sequence conferring resistance to *Bremia lactucae*, said selecting step comprising detecting (e.g., by genotyping) one or more of the following SNP markers:
   i) a G genotype in the heterozygous or homozygous state for SNP marker SL1831 in SEQ ID NO: 1;
   ii) an A genotype in the heterozygous or homozygous state for SNP marker SL1847 in SEQ ID NO: 6;
   iii) a G genotype in the heterozygous or homozygous state for SNP marker SL1887 in SEQ ID NO: 11; and/or
   iv) a C genotype in the heterozygous or homozygous state for SNP marker SL1883 in SEQ ID NO: 16;

thereby producing a plant with enhanced resistance to *Bremia lactucae*.

Optionally, the method further comprises:

c) selfing the selected progeny or crossing the selected progeny plant with another lettuce plant to produce further progeny. In embodiments, the further progeny are selected and selfed/crossed for 2 to 10 more generations.

In embodiments, said selecting step of b) comprises detecting (e.g., by genotyping) two or more, three or more, or all four of SNP markers SL1831, SL1847, SL1887 and/or SL1883.

Optionally, said selecting step comprises detecting at least the following SNP markers (either or both markers in heterozygous or homozygous form):

SL1831 and SL1847;
SL1831 and SL1883;
SL1831 and SL1887;
SL1847 and SL1883;
SL1847 and SL1887; or
SL1883 and SL1887.

In embodiments, markers SL1883 and SL1887 can be used together, optionally with the addition of other markers. As another exemplary illustration, markers SL1847 and SL1887 can be used in combination, optionally with the addition of other markers.

In embodiments, the first and/or second lettuce plants are *L. sativa* plants.

A further embodiment provides a method for producing a lettuce plant with enhanced resistance to *Bremia lactucae* (e.g., as compared with a control plant), the method comprising:

a) crossing a plant of *Lactuca serriola* accession CGN23091 with a second lettuce plant (e.g., a *L. sativa* plant) that lacks an introgressed sequence from *L. serriola* accession CGN23091 conferring resistance to *Bremia lactucae* to produce progeny plants;

b) selecting a progeny plant comprising an introgression on chromosome 2 from *L. serriola* accession CGN23091 that confers resistance to *Bremia lactucae*, said selecting step comprising detecting (e.g., by genotyping) one or more of the following SNP markers:
   i) a G genotype in the heterozygous or homozygous state for SNP marker SL1831 in SEQ ID NO: 1;
   ii) an A genotype in the heterozygous or homozygous state for SNP marker SL1847 in SEQ ID NO: 6;
   iii) a G genotype in the heterozygous or homozygous state for SNP marker SL1887 in SEQ ID NO: 11; and/or
   iv) a C genotype in the heterozygous or homozygous state for SNP marker SL1883 in SEQ ID NO: 16;

thereby producing a lettuce plant resistant to *Bremia lactucae*.

Optionally, the method further comprises:

c) selfing the selected progeny plant or crossing the selected progeny with another lettuce plant (e.g., a *L. sativa* plant) to produce further progeny. In embodiments, the further progeny are selected and selfed/crossed for 2 to 10 more generations.

In embodiments, said selecting step of b) comprises detecting (e.g., by genotyping) two or more, three or more, or all four of SNP markers SL1831, SL1847, SL1887 and/or SL1883.

Optionally, said selecting step comprises detecting at least the following SNP markers (either or both markers in the heterozygous or homozygous form):

SL1831 and SL1847;
SL1831 and SL1883;
SL1831 and SL1887;
SL1847 and SL1883;
SL1847 and SL1887; or
SL1883 and SL1887.

In embodiments, markers SL1883 and SL1887 can be used together, optionally with the addition of other markers. As another exemplary illustration, markers SL1847 and SL1887 can be used in combination, optionally with the addition of other markers.

In further embodiments, the invention provides a method for producing a F1 hybrid lettuce plant having enhanced resistance to *Bremia lactucae* (e.g., as compared with a control plant), the method comprising crossing a plant according to the present invention, which is an inbred lettuce (e.g., *Lactuca sativa*) plant, with a different inbred lettuce (e.g., *L. sativa*) plant to produce F1 hybrid lettuce progeny. According to the method, the second inbred lettuce plant may or may not comprise an introgressed sequence according to the invention conferring *Bremia* resistance.

In embodiments, the invention provides a method for identifying a lettuce plant (e.g., *L. sativa* plant) having enhanced resistance to *Bremia lactucae* (e.g., as compared with a control plant), said method comprising the step of detecting (e.g., by genotyping) one or more of the following SNP markers:

a) a G genotype in the heterozygous or homozygous state for SNP marker SL1831 in SEQ ID NO: 1;
b) an A genotype in the heterozygous or homozygous state for SNP marker SL1847 in SEQ ID NO: 6;
c) a G genotype in the heterozygous or homozygous state for SNP marker SL1887 in SEQ ID NO: 11; and/or
d) a C genotype in the heterozygous or homozygous state for SNP marker SL1883 in SEQ ID NO: 16;

thereby identifying a lettuce plant having enhanced resistance to *Bremia lactucae*.

In embodiments, the foregoing method further comprises selecting a lettuce plant comprising said one or more SNP markers, and crossing the selected lettuce plant with a second lettuce plant (e.g., a *L. sativa* plant), which may be the same or a different lettuce plant, to produce a progeny lettuce plant that comprises the one or more molecular markers and has enhanced resistance to *Bremia lactucae*. In embodiments, said detecting step comprises detecting by genotyping two or more, three or more, or all four of SNP markers SL1831, SL1847, SL1887 and/or SL1883. Optionally, said detecting step comprises detecting at least the following SNP markers (either or both markers in heterozygous or homozygous form):

SL1831 and SL1847;
SL1831 and SL1883;
SL1831 and SL1887;
SL1847 and SL1883;

SL1847 and SL1887; or
SL1883 and SL1887.

In embodiments, markers SL1883 and SL1887 can be used together, optionally with the addition of other markers. As another exemplary illustration, markers SL1847 and SL1887 can be used in combination, optionally with the addition of other markers.

As yet another embodiment, the invention provides a method of producing lettuce seed (e.g., *L. sativa* seed), the method comprising growing a lettuce plant from a seed according to the present invention, allowing the plant to produce further lettuce seed, and optionally collecting the further lettuce seed.

In another embodiment the invention relates to a method of providing a lettuce plant, plant part (e.g., leaf and/or head) or seed with enhanced resistance to *Bremia*, wherein said method comprises the following steps:

a) crossing a first lettuce plant (e.g., *L. sativa* plant) lacking the *Bremia* resistance-conferring introgressed sequence of the invention with a second lettuce plant (e.g., a *L. sativa* plant) according to any embodiment of the invention,
b) obtaining a progeny lettuce plant, and,
c) optionally, selecting a plant of said progeny characterized in that said progeny plant exhibits enhanced resistance to *Bremia* resistance.

According to the preceding embodiment, optionally, the second lettuce plant is a plant of *L. serriola* accession CGN23091 or *L. sativa* 18LEN002364, or a progeny or an ancestor thereof.

In another embodiment the invention relates to a method of identifying a lettuce plant (e.g., a *L. sativa* plant) comprising a *Bremia* resistance-conferring introgressed sequence of the invention, wherein said method comprises the steps of:

a) providing a lettuce (e.g., *L. sativa*) population segregating for the *Bremia* resistance trait;
b) screening the segregating population for a plant exhibiting resistance to *Bremia*, wherein said resistance trait can be identified by the presence of a *Bremia* resistance-conferring introgressed sequence of the invention; and
c) selecting a plant from the segregating population, wherein said plant comprises the *Bremia* resistance trait.

These and other aspects of the invention are described in more detail in the description of the invention that follows.

DETAILED DESCRIPTION OF THE INVENTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

All publications, patent applications, patents and other references cited herein are incorporated by reference in their entireties for the teachings relevant to the sentence and/or paragraph in which the reference is presented.

Nucleotide sequences provided herein are presented in the 5' to 3' direction, from left to right and are presented using the standard code for representing nucleotide bases as set forth in 37 CFR §§ 1.821-1.825 and the World Intellectual Property Organization (WIPO) Standard ST.25, for example: adenine (A), cytosine (C), thymine (T), and guanine (G).

Amino acids are likewise indicated using the WIPO Standard ST.25, for example: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Definitions

The technical terms and expressions used within the scope of this application are generally to be given the meaning commonly applied to them in the pertinent art of plant breeding and cultivation if not otherwise indicated herein below.

As used in this specification and the appended claims, the singular forms “a”, “an”, and “the” include plural referents unless the context clearly dictates otherwise. Thus, for example, reference to “a plant” includes one or more plants, and reference to “a cell” includes mixtures of cells, tissues, and the like.

As used herein, the term “about” when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, a “lettuce” plant refers to any plant in the genus *Lactuca*, including but not limited to *L. sativa, L. saligna, L. virosa*, and *L. serriola*. In embodiments, the lettuce plant is a *L. sativa*. In embodiments, the lettuce plant is cultivated.

A “cultivated lettuce” plant is understood within the scope of the invention to refer to a plant that is no longer in the natural state but has been developed and domesticated by human care and for agricultural use and/or human consumption, and excludes wild lettuce accessions, such as *L. serriola* accession CGN23091. As a matter of example, in embodiments, the stems and/or leaves of a cultivated lettuce plant do not have spines and have a closed flower.

Alternatively or additionally, the cultivated lettuce plant is a hybrid plant. Alternatively or additionally, the cultivated lettuce plant is a *L. sativa* plant. In the context of an interspecific cross between a *L. sativa* plant and a wild lettuce, a progeny plant of said interspecific cross is considered a "cultivated lettuce" plant when said progeny plant has been backcrossed at least three times against a *L. sativa* plant.

An "allele" is understood within the scope of the invention to refer to alternative or variant forms of a gene or other genetic element. Such alternative or variant forms may be the result of single nucleotide polymorphisms, insertions, inversions, translocations or deletions, or the consequence of gene regulation caused by, for example, by chemical or structural modification, transcription regulation or post-translational modification/regulation. In a diploid cell or organism, the two alleles of a given gene or genetic element typically occupy corresponding loci on a pair of homologous chromosomes.

"*Bremia lactucae*". An Oomycete that causes downy mildew in lettuce, particularly in cooler growing regions.

As used herein, the term "resistance" and "resistant" (and like terms) refers to the ability of a plant to restrict the growth and development of a specified pathogen and/or the damage caused by the pathogen when compared to susceptible plants under similar environmental conditions and pathogen pressure. Resistance can be qualitative or quantitative. In embodiments, a "resistant" plant exhibits reduced, essentially no, or even no symptoms to a specific pathogen. In some embodiments, "resistant" plants show some symptoms but are still able to produce marketable product with an acceptable yield, e.g., the yield may be reduced and/or the plants may be stunted as compared with the yield and/or growth in the absence of the pathogen. In embodiments, a lettuce plant according to the invention is resistant to at least *Bremia lactucae* races BI 16-36EU as characterized and classified according to SEXTET code by IBEB (International *Bremia* Evaluation Board). In embodiments, a *Bremia* resistant lettuce plant of the invention exhibits no or very few necroses with no or very sparse sporulation under standard test conditions, for example, the test conditions defined in Example 1 below, e.g., when inoculated with any of *Bremia* races BI 16-36EU. In embodiments, the *Bremia* resistance of the invention is dominant. In embodiments, the *Bremia* resistance is qualitative. In embodiments, the *Bremia* resistance of the invention exhibits monogenic inheritance.

The term "enhanced *Bremia* resistance" (and like terms) is herein understood to mean that a plant is more resistant to at least one *Bremia* race or isolate (e.g., a statistically significant improvement in *Bremia* resistance as compared with a control lettuce plant not comprising an introgressed sequence of the invention, at $p<0.1$, $p<0.05$ or $p<0.01$ using Student's test) and/or has a broader spectrum of *Bremia* resistance (e.g., has resistance against one or more additional *Bremia* races/isolates) as compared with a control lettuce plant not comprising an introgressed sequence of the invention. In embodiments, "enhanced *Bremia* resistance" refers to the provision of an additional resistance against one or more *Bremia* races or isolates that the plant may already have had (i.e., stacking of resistance), thereby lowering the risk of the *Bremia* resistance being broken as compared with a plant lacking said introgressed sequence (i.e., as a form of resistance management).

A "control lettuce plant" is understood within the scope of the invention to mean a lettuce plant of the same species as the lettuce plant of the invention (e.g., *L. sativa*) and does not have the introgressed sequence of the present invention linked to *Bremia* resistance (e.g., one of the parent lettuce plants that does not have an introgressed sequence of the invention). In embodiments, the control lettuce plant has the same genetic background as the lettuce plant of the present invention, and optionally is a plant belonging to the same plant variety that does not comprise the introgressed sequence of the present invention. Plant variety is herein understood according to definition of UPOV. Thus, a control lettuce plant may be a near-isogenic line, an inbred line or a hybrid provided that they have the same genetic background as the lettuce plant of the present invention except the control plant does not have the introgressed sequence of the present invention linked to *Bremia* resistance. The control lettuce plant is grown for the same length of time and under the same conditions as the lettuce plant of the invention.

The term "trait" refers to a characteristic or a phenotype (e.g., a disease resistance such as *Bremia* resistance). A trait may be inherited in a dominant or recessive manner, or in a partial or incomplete-dominant manner. In the context of the present invention, the *Bremia* resistance of the present invention is a dominant trait. A lettuce plant of the invention can therefore be homozygous or heterozygous for the trait. Furthermore, a trait may be monogenic or polygenic, or may result from the interaction of one or more genes with the environment. In the context of the present invention, the *Bremia* resistance-conferring introgressed sequence located on chromosome 2, exhibits monogenic inheritance, and is sufficient to confer the *Bremia* resistance trait.

The terms "hybrid", "hybrid plant", and "hybrid progeny" refer to an individual produced from genetically different parents (e.g., a genetically heterozygous or mostly heterozygous individual).

The term "inbred line" refers to a genetically homozygous or nearly homozygous population. An inbred line, for example, can be derived through several cycles of brother/sister breeding or of selfing or by dihaploid production.

The term "dihaploid line" refers to stable inbred lines issued from anther culture. Some pollen grains (haploid) cultivated on specific medium and circumstances can develop plantlets containing n chromosomes. These plantlets are then "doubled" and contain 2n chromosomes. The progeny of these plantlets are named "dihaploid" and are essentially no longer segregating (stable).

The term "cultivar" or "variety" refers to a horticulturally created variety, as distinguished from a naturally occurring variety. In some embodiments of the present invention the cultivars or varieties are commercially valuable.

The term "genetically fixed" refers to a genetic element that has been stably incorporated into the genome of a plant that normally does not contain the genetic element. When genetically fixed, the genetic element can be transmitted in an easy and predictable manner to other plants by sexual crosses.

The term "plant" or "plant part' refers herein to a plant part, organ or tissue obtainable from a plant according to the invention, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, heads, cores, cell or tissue cultures (including callus cultures) or any other part or product of the plant. In embodiments, the plant part comprises the introgressed sequence of the invention. In embodiments, the plant part exhibits the *Bremia* resistance trait according to the invention, particularly when grown into a plant that produces lettuce leaves and/or heads.

A "plant" is any plant at any stage of development.

A plant "seed" is a seed that grows into a plant according to any of the embodiments.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant. "Plant cell culture" means cultures of plant units such as, for example, protoplasts, cell culture cells, cells in plant tissues, pollen, pollen tubes, ovules, embryo sacs, zygotes and embryos at various stages of development.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

"Processed food" is understood within the scope of the invention to mean food that has been altered from its natural state. Methods used for processing food include but are not limited to cutting, slicing, dicing, grinding, canning, freezing, refrigeration, dehydration, heating and aseptic processing.

"Fresh cut market" is understood within the scope of the invention to mean vegetables on the market that have been minimally processed.

As used herein, the term "marker allele" or "allele of a marker locus" (and similar terms) refers to an allele (as defined herein) at a polymorphic locus that is used as a marker to locate and/or indicate the presence of one or more genetically linked loci that contribute to variability of a phenotypic trait(s) (e.g., a *Bremia* resistance locus).

As used herein, "marker locus" refers to a region on a chromosome that comprises a nucleotide or a polynucleotide sequence that is present in an individual's genome and that is genetically linked with one or more loci of interest, which may comprise a gene or any other genetic determinant or factor contributing to a trait. "Marker locus" also refers to a region on a chromosome that comprises a polynucleotide sequence complementary to a genomic sequence, such as a sequence of a nucleic acid used as a probe. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the term "breeding", and grammatical variants thereof, refers to any process that generates a progeny individual. Breeding can be sexual or asexual, or any combination thereof. Exemplary non-limiting types of breeding include crossings, selfing, doubled haploid derivative generation, and combinations thereof.

As used herein, the phrase "established breeding population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

As used herein, the term "diploid" plant refers to a plant that has two sets of chromosomes, typically one from each of its two parents. However, it is understood that in some embodiments a diploid plant can receive its "maternal" and "paternal" sets of chromosomes from the same single organism, such as when a plant is selfed to produce a subsequent generation of plants.

"Homozygous" is understood within the scope of the invention to refer to like alleles at one or more corresponding loci on homologous chromosomes.

"Heterozygous" is understood within the scope of the invention to refer to unlike alleles at one or more corresponding loci on homologous chromosomes.

A "dominant" allele is understood within the scope of the invention to refer to an allele that determines the phenotype when present in the heterozygous or homozygous state.

A "recessive" allele refers to an allele that determines the phenotype only when present in the homozygous state.

"Backcrossing" is understood within the scope of the invention to refer to a process in which a hybrid progeny is repeatedly crossed back to one of the parents (the "recurrent" parent). Different recurrent parents may be used in subsequent backcrosses.

"Locus" is understood within the scope of the invention to refer to a region on a chromosome, which comprises a gene or any other genetic element or factor contributing to a trait.

"Genetic linkage" is understood within the scope of the invention to refer to an association of characters in inheritance due to location of genes in proximity on the same chromosome, measured by percent recombination between loci (centi-Morgan, cM).

For the purpose of the present invention, the term "co-segregation" refers to the fact that the allele for the trait and the allele(s) for the marker(s) tend to be transmitted together because they are physically close together on the same chromosome (i.e., reduced recombination between them because of their physical proximity) resulting in a non-random association of their alleles as a result of their proximity on the same chromosome. The term "associated with" can be used with an equal meaning.

As used herein, the term "genetic architecture at the quantitative/qualitative trait locus" refers to a genomic region which is statistically correlated to the phenotypic trait of interest and represents the underlying genetic basis of the phenotypic trait of interest.

As used herein, the phrase "genetic marker" or "molecular marker" refer to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of a phenotypic trait(s). The phrase "genetic marker" can also refer to a polynucleotide sequence complementary to a genomic sequence, such as a sequence of a nucleic acid used as a probe. In embodiments, a genetic marker can be physically located in a position on a chromosome that is within or outside the genetic locus with which it is associated (i.e., is intragenic or extragenic, respectively).

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more genes are involved in the expression of a phenotype of interest (e.g., a quantitative trait as defined herein). Thus, in some embodiments a genotype comprises one or more alleles present within an individual at one or more genetic loci. In some embodiments, a genotype is expressed in terms of a haplotype (also defined herein).

As used herein, the term "germplasm" refers to the totality of the genotypes of a population or other group of individuals (e.g., a species). The term "germplasm" can also refer to plant material; e.g., a group of plants that act as a repository for various alleles. The phrase "adapted germplasm" refers to plant materials of proven genetic superiority; e.g., for a given environment or geographical area, while the phrases "non-adapted germplasm," "raw germplasm," and "exotic germplasm" refer to plant materials of unknown or unproven genetic value, e.g., for a given environment or geographical area. As such, the phrase "non-adapted germplasm" refers in some embodiments to plant materials that are not part of an established breeding population and that do not have a known relationship to a member of the established breeding population.

A "haplotype" is the genotype of an individual at a plurality of genetic loci, i.e., a combination of alleles. Typically, the genetic loci that define a haplotype are physically and genetically linked, i.e., multiple loci along the same chromosome segment.

As used herein, the terms "introgression," "introgressing" and "introgressed" (and grammatical variants thereof) refer to both the natural and artificial transmission of a desired allele or combination of desired alleles of a genetic locus or genetic loci from one genetic background to another. For example, a desired allele at a specified locus can be transmitted to at least one progeny via a sexual cross between two parents, where at least one of the parents has the desired allele in its genome (the "donor" parent). Alternatively, for example, transmission of an allele can occur by recombination between two donor genomes, e.g., in a fused protoplast, where at least one of the donor protoplasts has the desired allele in its genome. Offspring comprising the desired allele can be repeatedly backcrossed to a recurrent parent to create a line having a desired genetic background and selected for the desired allele, with the result being that the desired allele becomes fixed in the desired genetic background. For example, a marker associated with enhanced *Bremia* resistance may be introgressed from a donor parent into a recurrent parent that does not comprise the introgressed sequence. The resulting offspring can optionally be repeatedly backcrossed to the recurrent parent and selected until the progeny possess the introgressed sequence conferring *Bremia* resistance in the recurrent parent background.

As used herein, the term "linkage", and grammatical variants thereof, refers to the tendency of alleles at different loci on the same chromosome to segregate together more often than would be expected by chance if their transmission were independent, in some embodiments as a consequence of their physical proximity.

As used herein, the phrase "nucleic acid" refers to any physical string of monomer units that can be corresponded to a string of nucleotides, including a polymer of nucleotides (e.g., a typical DNA, cDNA or RNA polymer), modified oligonucleotides (e.g., oligonucleotides comprising bases that are not typical to biological RNA or DNA, such as 2'-O-methylated oligonucleotides), and the like. In some embodiments, a nucleic acid can be single-stranded, double-stranded, multi-stranded, or combinations thereof. Unless otherwise indicated, a particular nucleic acid sequence of the presently disclosed subject matter optionally comprises and/or encodes complementary sequences, in addition to any sequence explicitly indicated.

As used herein, the term "plurality" refers to more than one. Thus, a "plurality of individuals" refers to at least two individuals. In some embodiments, the term plurality refers to more than half of the whole. For example, in some embodiments a "plurality of a population" refers to more than half the members of that population. These usages of the term "plurality" will be apparent to those skilled in the art depending on context.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be of any generation, for example, of the $F_1$, the $F_2$, or any subsequent generation.

As used herein, the phrase "qualitative trait" refers to a phenotypic trait that is controlled by one or a few genes that exhibit major phenotypic effects. Because of this, qualitative traits are typically simply inherited. Examples in plants include, but are not limited to, flower colour, and several known disease resistances such as, for example, the *Bremia* resistance of the present invention.

As used herein, the phrase "quantitative trait" refers to a phenotypic trait that can be described numerically (i.e., quantitated or quantified). A quantitative trait typically exhibits continuous variation between individuals of a population; that is, differences in the numerical value of the phenotypic trait are slight and grade into each other. Frequently, the frequency distribution in a population of a quantitative phenotypic trait exhibits a bell-shaped curve (i.e., exhibits a normal distribution between two extremes). A "quantitative trait" is typically the result of a genetic locus interacting with the environment or of multiple genetic loci interacting with each other and/or with the environment. Examples of quantitative traits include plant height and yield.

As used herein, the terms "quantitative trait locus" (QTL) and "marker trait association" refer to an association between a genetic marker and a chromosomal region and/or gene that affects the phenotype of a trait of interest. Typically, this is determined statistically; e.g., based on one or more methods published in the literature. A QTL can be a chromosomal region and/or a genetic locus with at least two alleles that differentially affect a phenotypic trait (either a quantitative trait or a qualitative trait).

The term "recipient plant" is used herein to indicate a plant that is to receive DNA obtained from a donor plant that comprises an introgressed sequence for a trait of interest (e.g., *Bremia* resistance). Said "recipient plant" may or may not already comprise one or more native or introgressed sequences for *Bremia* resistance, in which case the term indicates a plant that is to receive an additional introgressed sequence at a different locus.

The term "natural genetic background" is used herein to indicate the original genetic background of a genetic sequence of interest. Such a genetic background may for instance be the genome of a wild accession. For instance, the genetic sequences of the present invention were found at specific locations on chromosome 2 of a *L. serriola* plant. Conversely, a method that involves the transfer of DNA, via e.g. breeding, comprising this genetic sequence from e.g. chromosome 2 of a *L. serriola* plant to the same position on chromosome 2 of another lettuce species (e.g., *L. sativa*), will result in this genetic sequence not being in its natural genetic background. When the genetic sequences of the present invention are transferred from a *L. serriola* background into another lettuce species (e.g., *L. sativa*), they are referred to as an "introgressed sequence" or "introgressed genetic sequence" (or similar terms).

A "donor plant" is understood within the scope of the invention to mean the plant that provides at least one sequence for enhanced *Bremia* resistance (i.e., to be introgressed into the recipient plant).

"Marker-based selection" is understood within the scope of the invention to refer to, e.g., the use of genetic markers to detect one or more nucleic acids from the plant, where the nucleic acid is associated with a desired trait to identify plants that carry an allele(s) conferring desirable (or undesirable) traits, so that those plants can be used (or avoided) in a selective breeding program.

A single nucleotide polymorphism (SNP), a variation at a single site in DNA, is the most frequent type of variation in the genome. A SNP is a DNA sequence variation occurring when a single nucleotide—A, T, C, or G—in the genome (or other shared sequence) differs between members of a biological species or paired chromosomes in an individual. For example, two sequenced DNA fragments from different individuals, AAGCCTA to AAGCTTA, contain a difference in a single nucleotide. In this case there are two alleles: C and T. The basic principles of SNP array are the same as the DNA microarray. These are the convergence of DNA hybridization, fluorescence microscopy, and DNA capture. The three components of the SNP arrays are: the array that contains nucleic acid sequences (e.g., amplified sequence or target), one or more labelled allele-specific oligonucleotide probes, and a detection system that records and interprets the hybridization signal. The presence or absence of the desired allele may be determined, e.g., by real-time PCR using double-stranded DNA dyes or the fluorescent reporter probe method.

"PCR (Polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

"Phenotype" is understood within the scope of the invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

"Polymorphism" is understood within the scope of the invention to refer to the presence in a population of two or more different forms of a gene, genetic marker, or inherited trait or a gene product obtainable, for example, through alternative splicing, DNA methylation, etc.

"Probe" as used herein refers to a group of atoms or molecules that is capable of recognising and binding to a specific target molecule or cellular structure and thus allowing detection of the target molecule or structure. In embodiments, a "probe" refers to a labelled DNA or RNA sequence that can be used to detect the presence of and to quantitate a complementary sequence by molecular hybridization.

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" is in some embodiments fertilization of one individual by another (e.g., cross-pollination in plants).

"Selective breeding" is understood within the scope of the invention to refer to a program of breeding that uses plants that possess or display desirable traits as parents.

The term "selfing" refers in some embodiments to the production of seed by self-fertilization or self-pollination; i.e., pollen and ovule are from the same plant.

"Tester" plant is understood within the scope of the invention to refer to a plant of the genus *Solanum* used to characterize genetically a trait in a plant to be tested. Typically, the plant to be tested is crossed with a "tester" plant and the segregation ratio of the trait in the progeny of the cross is scored.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al. loc. cit.). High stringency hybridization conditions as for instance described in Sambrook et al, supra, are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

In accordance with the present invention, the term "said position corresponding to position X", X being any number to be found in the respective context in the present application, does not only include the respective position in the SEQ ID NO referred to afterwards but also includes any sequence encoding a genetic sequence of the invention, where, after alignment with the reference SEQ ID NO, the respective position might have a different number but corresponds to that indicated for the reference SEQ ID NO.

Alignment of genetic sequences can be effected by applying various alignment tools known to the person skilled in the art.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point for the specific sequence at a defined ionic strength and pH. Typically, under "stringent conditions" a probe will hybridize to its target subsequence, but to no other sequences.

The "thermal melting point" is the temperature (under defined ionic strength and pH) at which 50% of the target sequence hybridizes to a perfectly matched probe. Very stringent conditions are selected to be equal to the melting temperature (Tm) for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2 times SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1 times SSC at 45° C. for 15 minutes. An example low stringency wash for a duplex of, e.g., more than 100 nucleotides, is 4-6 times SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2 times (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g. when a copy of a nucleic acid is created using the maximum codon degeneracy permitted by the genetic code.

Plants, Seeds, Products.

In a first embodiment, the invention provides a lettuce plant (e.g., a *Lactuca sativa* plant) having enhanced resistance to *Bremia lactucae* (e.g., as compared with a control plant) comprising an introgressed sequence from *Lactuca serriola* that confers a resistance to *Bremia lactucae*, wherein said introgressed sequence is comprised in a *Lactuca serriola* accession (e.g., accession CGN23091) or in deposited *Lactuca sativa* line 18LEN002364 and wherein said introgressed sequence is located on chromosome 2. In embodiments, the resistance is a qualitative resistance. In embodiments, the resistance is a qualitative resistance. In embodiments, the resistance exhibits monogenic inheritance.

In embodiments, the plant of the invention is a cultivated plant, optionally a cultivated *L. sativa* plant.

In embodiments, said introgressed sequence confers resistance at least against *Bremia lactucae* races BI 16-36EU.

In embodiments, the introgressed sequence comprises one or more of the SNP markers shown in Table 3 herein. In embodiments, the introgression comprises one or more, two or more, three or more or all four of the following SNP markers:

a) a G genotype in the heterozygous or homozygous state for SNP marker SL1831 in SEQ ID NO: 1;
b) an A genotype in the heterozygous or homozygous state for SNP marker SL1847 in SEQ ID NO: 6;
c) a G genotype in the heterozygous or homozygous state for SNP marker SL1887 in SEQ ID NO: 11; and/or
d) a C genotype in the heterozygous or homozygous state for SNP marker SL1883 in SEQ ID NO: 16.

In a further embodiment:

a) the G genotype for marker SL1831 can be identified in a PCR by amplification of a nucleic acid fragment with a pair of oligonucleotide primers: forward primer of SEQ ID NO: 2 and reverse primer of SEQ ID NO: 5, and probe of SEQ ID NO: 3;
b) the A genotype for SNP marker SL1847 can be identified in a PCR by amplification of a nucleic acid fragment with a pair of oligonucleotide primers: forward primer of SEQ ID NO: 7 and reverse primer of SEQ ID NO: 10, and probe of SEQ ID NO: 8;
c) the G genotype for SNP marker SL1887 can be identified in a PCR by amplification of a nucleic acid fragment with a pair of oligonucleotide primers: forward primer of SEQ ID NO: 12 and reverse primer of SEQ ID NO: 15, and probe of SEQ ID NO: 13; and
d) the C genotype for SNP marker SL1883 can be identified in a PCR by amplification of a nucleic acid fragment with a pair of oligonucleotide primers: forward primer of SEQ ID NO: 17 and reverse primer of SEQ ID NO: 20, and probe of SEQ ID NO: 18.

In representative embodiments, the plant of the invention comprises at least the following SNP markers (each individual marker being present in heterozygous or homozygous form):

SL1831 and SL1847;
SL1831 and SL1883;
SL1831 and SL1887;
SL1847 and SL1883;
SL1847 and SL1887;
SL1883 and SL1887;
SL1831, SL1847 and SL1883;
SL1831, SL1847 and SL1887;
SL1847, SL1883 and SL1887; or
SL1831, SL1847, SL1883 and SL1887.

For example, markers SL1883 and SL1887 can be used together, optionally with the addition of other markers. As another exemplary illustration, markers SL1847 and SL1887 can be used in combination, optionally with the addition of other markers.

In representative embodiments, the introgressed sequence comprises one or more, two or more, three or more or all four of SEQ ID NO: 1 having a resistance marker allele represented by nucleotide G at position 112, SEQ ID NO: 6 having a resistance marker allele represented by nucleotide A at position 112, SEQ ID NO: 11 having a resistance marker allele represented by nucleotide G at position 99 and/or SEQ ID NO: 16 having a resistance marker allele represented by nucleotide C at position 41, or a sequence that is at least 80%, 85%, 90%, 95%, 96%, 97%, 98%, or 99% identical to one or more of the foregoing sequences and comprises the resistance marker allele.

In a further embodiment, the invention provides a plant according to any of the embodiments described herein wherein said plant comprises at least one copy (e.g., is heterozygous) of said *Bremia* resistance-conferring introgressed sequence.

In a further embodiment, the invention provides a plant according to any of the preceding embodiments wherein said plant comprises two copies (e.g., said plant is homozygous) of said *Bremia* resistance-conferring introgressed sequence.

In a further embodiment, the plant of the invention is an inbred, a dihaploid or a hybrid plant.

In embodiments, the invention provides plant of deposited *Lactuca sativa* line 18LEN002364.

In a further embodiment, the invention provides a seed that produces a plant according to the invention.

In a further embodiment, the invention provides a seed produced by a plant according to the invention.

In a further embodiment, the lettuce plant of the invention is a lettuce plant according to any embodiment described herein, wherein *L. sativa* line 18LEN002364, or a progeny or an ancestor thereof, is the source of said *Bremia* resistance-conferring introgressed sequence.

In a further embodiment, the lettuce plant of the invention is a lettuce plant according to any of the preceding embodiments, wherein *L. serriola* accession CGN23091, or a progeny or an ancestor thereof, is the source of said *Bremia* resistance-conferring introgressed sequence.

In a further embodiment, the lettuce plant of the invention is a lettuce plant according to any of preceding embodiments, wherein said plant is obtained by crossing *L. serriola* accession CGN23091 or *L. sativa* 18LEN002364, or a progeny or an ancestor thereof, with a lettuce plant that does not contain said *Bremia* resistance-conferring introgressed sequence.

It is a further embodiment to provide a plant part, organ or tissue obtainable from a lettuce plant according to any of preceding embodiments, including but not limiting to leaves, cores, heads, stems, roots, flowers or flower parts, shoots, gametophytes, sporophytes, pollen, anthers, microspores, egg cells, zygotes, embryos, meristematic regions, callus tissue, seeds, cuttings, cell or tissue cultures or any other part or product of the plant. In embodiments, the plant part, organ or tissue comprises the introgressed sequence that confers *Bremia* resistance. In embodiments, the plant part, organ or tissue exhibits the *Bremia* resistance according to the invention, particularly when grown into a plant that produces lettuce heads and/or leaves.

In another embodiment is considered the use of a lettuce plant, plant part or seed according to any of the preceding embodiments for producing, and optionally harvesting, a lettuce head and/or leaves.

In another embodiment the invention relates to the use of a lettuce plant, plant part or seed according to any embodiment of the invention, wherein the lettuce plant, plant part or seed is *L. sativa* 18LEN002364, or a progeny or an ancestor thereof.

In a further embodiment the invention relates to the use of a lettuce plant, plant part or seed according to any of the embodiments of the invention to sow a field, a greenhouse, or a plastic house.

In another embodiment, the plant according to the invention is male sterile.

In another embodiment, the plant according to the invention grows mature lettuce heads and/or leaves.

In one embodiment, the invention provides lettuce leaves and heads produced by a lettuce plant according to any of the embodiments of the invention.

The present invention further relates to a lettuce plant seed, particularly a cultivated lettuce plant seed (e.g., a *L. sativa* seed) that grows into a lettuce plant according to any of the embodiments of the invention.

The invention further relates to the use of a lettuce plant according to any of the embodiments to introduce (e.g., introgress) a *Bremia* resistance trait of the invention into a lettuce plant (e.g., a *L. sativa* plant) lacking said *Bremia* resistance trait.

Genetic Sequences, Markers.

The present invention is further directed to a genetic sequence directing or controlling expression of the *Bremia* resistance trait in the lettuce plant. In a further embodiment, the genetic sequence of the present invention is located on chromosome 2. In a further embodiment of the present invention, the genetic sequence is obtainable from a donor plant that has the genetic background of *L. sativa* 18LEN002364, or a progeny or an ancestor thereof, and comprising said genetic sequence.

In a further embodiment, the genetic sequence of the present invention is genetically or physically linked to one or more marker loci, which co-segregate with the *Bremia* resistance trait.

In another embodiment, said genetic sequences of the present invention are characterized by one or more SNP markers as described in Table 3, for example, one or more, two or more, three or more or all four of SNP markers SL1831, SL1847, SL1883 and SL1887 comprising:

a) a G genotype in the heterozygous or homozygous state for SNP marker SL1831 in SEQ ID NO: 1;
b) an A genotype in the heterozygous or homozygous state for SNP marker SL1847 in SEQ ID NO: 6;
c) a G genotype in the heterozygous or homozygous state for SNP marker SL1887 in SEQ ID NO: 11; and/or
d) a C genotype in the heterozygous or homozygous state for SNP marker SL1883 in SEQ ID NO: 16.

In representative embodiments:

a) the G genotype for marker SL1831 can be identified in a PCR by amplification of a nucleic acid fragment with a pair of oligonucleotide primers: forward primer of SEQ ID NO: 2 and reverse primer of SEQ ID NO: 5, and probe of SEQ ID NO: 3;
b) the A genotype for SNP marker SL1847 can be identified in a PCR by amplification of a nucleic acid fragment with a pair of oligonucleotide primers: forward primer of SEQ ID NO: 7 and reverse primer of SEQ ID NO: 10, and probe of SEQ ID NO: 8;
c) the G genotype for SNP marker SL1887 can be identified in a PCR by amplification of a nucleic acid fragment with a pair of oligonucleotide primers: forward primer of SEQ ID NO: 12 and reverse primer of SEQ ID NO: 15, and probe of SEQ ID NO: 13; and
d) the C genotype for SNP marker SL1883 can be identified in a PCR by amplification of a nucleic acid fragment with a pair of oligonucleotide primers: forward primer of SEQ ID NO: 17 and reverse primer of SEQ ID NO: 20, and probe of SEQ ID NO: 18.

In a further embodiment, the present invention discloses a kit for the detection (e.g., by genotyping) of the *Bremia* resistance trait locus of the invention in a lettuce plant, optionally a cultivated *L. sativa* lettuce plant, wherein said kit comprises at least one PCR oligonucleotide primer pair and probe, selected from:

i. a primer pair represented by a forward primer of SEQ ID NO: 2 and a reverse primer of SEQ ID NO: 5, and probe of SEQ ID NO: 3;

ii. a primer pair represented by a forward primer of SEQ ID NO: 7 and a reverse primer of SEQ ID NO: 10, and probe of SEQ ID NO: 8;

iii. a primer pair represented by a forward primer of SEQ ID NO: 12 and a reverse primer of SEQ ID NO: 15, and probe of SEQ ID NO: 13; and/or iv. a primer pair represented by a forward primer of SEQ ID NO: 17 and a reverse primer of SEQ ID NO: 20, and probe of SEQ ID NO: 18.

The present invention also discloses the use of the SNP markers according to the invention for diagnostic selection and/or genotyping of the *Bremia* resistance trait locus in a lettuce plant, particularly a cultivated lettuce plant (e.g., a *L. sativa*)

The present invention further discloses the use of some or all of these DNA markers for identifying in a lettuce plant, particulary a cultivated lettuce plant, more particularly a *L. sativa* lettuce plant according to the invention, the presence of a *Bremia* resistance trait locus and/or for monitoring the introgression of the *Bremia* resistance trait locus in a lettuce plant, particularly a cultivated lettuce plant, particularly a *L. sativa* lettuce plant according to the invention and as described herein.

The invention further discloses a polynucleotide (amplification product) obtainable in a PCR reaction involving at least one oligonucleotide primer disclosed herein: SEQ ID NO: 2, SEQ ID NO: 5, SEQ ID NO: 7, SEQ ID NO: 10, SEQ ID NO: 12, SEQ ID NO: 15, SEQ ID NO: 17 or SEQ ID NO: 20, and reacting with probes of SEQ ID NO: 3, SEQ ID NO: 8, SEQ ID NO: 13 and/or SEQ ID NO: SEQ ID NO: 18, respectively. The invention also provides a polynucleotide (amplification product) obtainable in a PCR reaction involving a pair of PCR oligonucleotide primers selected from: SEQ ID NO: 2 and SEQ ID NO: 5; SEQ ID NO: 7 and SEQ ID NO: 10; SEQ ID NO: 12 and SEQ ID NO: 15; or SEQ ID NO: 17 and SEQ ID NO: 20, and reacting with probes of SEQ ID NO: 3, SEQ ID NO: 8, SEQ ID NO: 13 or SEQ ID NO: SEQ ID NO: 18, respectively.

Also contemplated herein is a polynucleotide that has at least 90%, particularly at least 95%, particularly at least 96%, particularly at least 97%, particularly at least 98%, particularly at least 99% sequence identity with the sequence of said amplification product and/or a polynucleotide exhibiting a nucleotide sequence that hybridizes to the nucleotide sequence of said amplification product obtainable in the above PCR reaction.

In embodiments, the amplification product corresponds to an amplification product using the same primer/primer pair obtainable from *L. sativa* 18LEN002364, or a progeny or an ancestor thereof comprising the *Bremia* resistance-conferring introgressed sequence of the invention, or is at least 90%, 95%, 96%, 97%, 98% or 99% identical thereto.

The amplification product according to the invention and described herein can be used for generating or developing new primers and/or probes that can be used for identifying the *Bremia* resistance trait locus of the invention.

The present invention therefore further relates in one embodiment to derived markers, particularly to derived primers or probes, developed from an amplification product according to the invention and as described herein and by methods known in the art, which derived markers are genetically linked to the *Bremia* resistance trait locus of the invention.

Methods of Breeding.

The invention also provides a method for producing a lettuce plant having enhanced resistance to *Bremia lactucae* (e.g., as compared with a control). In embodiments, the method comprises:

a) crossing a first lettuce plant (e.g., a *L. sativa* plant, particularly a cultivated *L. sativa* plant) according to the invention with a second lettuce plant lacking the introgressed sequence of the invention conferring resistance to *Bremia lactucae* to produce progeny plants; and b) selecting a progeny plant comprising said introgressed sequence conferring resistance to *Bremia lactucae;* thereby producing a plant with enhanced resistance to *Bremia lactucae.*

In embodiments, said selecting step comprises detecting (e.g., by genotyping) one or more, two or more, three or more, or all four of the following SNP markers:

i) a G genotype in the heterozygous or homozygous state for SNP marker SL1831 in SEQ ID NO: 1;

ii) an A genotype in the heterozygous or homozygous state for SNP marker SL1847 in SEQ ID NO: 6;

iii) a G genotype in the heterozygous or homozygous state for SNP marker SL1887 in SEQ ID NO: 11; and/or iv) a C genotype in the heterozygous or homozygous state for SNP marker SL1883 in SEQ ID NO: 16.

In embodiments, the first lettuce plant is a cultivated lettuce plant. In embodiments, the first lettuce plant is a *L. sativa* plant. In embodiments, the second lettuce plant is a *L. sativa* plant.

In embodiments of the methods according to the invention, the method comprises detecting (e.g., by genotyping) the resistance associated genotype (as described herein) at the following SNP markers(each individual marker being present in heterozygous or homozygous form):

SL1831 and SL1847;
SL1831 and SL1883;
SL1831 and SL1887;
SL1847 and SL1883;
SL1847 and SL1887;
SL1883 and SL1887;
SL1831, SL1847 and SL1883;
SL1831, SL1847 and SL1887;
SL1847, SL1883 and SL1887; or
SL1831, SL1847, SL1883 and SL1887.

For example, markers SL1883 and SL1887 can be used together, optionally with the addition of other markers. As another exemplary illustration, markers SL1847 and SL1887 can be used in combination, optionally with the addition of other markers.

In a further embodiment, the invention relates to the method of any one of the embodiments described herein wherein the first lettuce plant of step a) is *L. serriola* accession CGN23091 or a progeny or an ancestor thereof comprising the introgressed sequence of the invention, and the second lettuce plant lacks an introgressed sequence of the invention conferring resistance to *Bremia lactucae.*

In a further embodiment, the invention relates to the method of any one of the embodiments described herein wherein the first lettuce plant of step a) is *L. sativa* 18LEN002364 or a progeny or an ancestor thereof comprising the introgressed sequence of the invention, and the second lettuce plant lacks an introgressed sequence of the invention conferring resistance to *Bremia lactucae.*

In embodiments, according to any of the embodiments of the invention, the method further comprises:

c) selfing the selected progeny plant or crossing with another lettuce plant to produce further progeny. In embodiments, further progeny are selected and selfed/crossed for 2 to 10 more generations.

As a further embodiment, the invention provides a method for producing a F1 hybrid lettuce plant with enhanced resistance to *Bremia lactucae* (e.g., as compared with a control plant), the method comprising crossing an inbred (including dihaploid) lettuce plant of the invention with a different inbred lettuce plant to produce F1 hybrid progeny. According to this method, the second lettuce plant may or may not comprise the introgressed sequence conferring *Bremia* resistance of the invention.

In embodiments, the first lettuce plant is a cultivated lettuce plant. In embodiments, the first lettuce plant is a *L. sativa* plant. In embodiments, the second lettuce plant is a *L. sativa* plant.

Methods of Selection.

In a further embodiment, the invention provides a method for identifying a lettuce plant resistant to *Bremia lactucae*, and comprising at least one copy of an introgressed sequence of the invention (i.e., the plant is heterozygous or homozygous), said method comprising the step of detecting (e.g., by genotyping) one or more, two or more, three or more, or all four of the following SNP markers:

a) a G genotype in the heterozygous or homozygous state for SNP marker SL1831 in SEQ ID NO: 1;
b) an A genotype in the heterozygous or homozygous state for SNP marker SL1847 in SEQ ID NO: 6;
c) a G genotype in the heterozygous or homozygous state for SNP marker SL1887 in SEQ ID NO: 11; and/or
d) a C genotype in the heterozygous or homozygous state for SNP marker SL1883 in SEQ ID NO: 16;

thereby identifying a lettuce plant resistant to *Bremia lactucae*.

In embodiments, the plant is a cultivated plant (e.g., a cultivated *L. sativa*).

In embodiments, the further comprises selecting a lettuce plant comprising said one or more SNP markers, and crossing the selected lettuce plant with a second lettuce plant to produce progeny lettuce plants that comprise the one or more molecular markers and are resistant to *Bremia lactucae* (e.g., comprise the introgressed sequence of the invention conferring *Bremia* resistance). In embodiments, the second lettuce plant is different from the selected lettuce plant. In embodiments, the second lettuce plant is a *L. sativa*. In embodiments, the second lettuce plant does not comprise the introgressed sequence conferring *Bremia* resistance of the invention. In embodiments, the second lettuce plant does comprise said introgressed sequence.

In another embodiment the invention relates to a method of identifying a lettuce plant comprising the *Bremia* resistance-conferring introgressed sequence of the invention, wherein said method comprises the steps of:

a) providing a population segregating for the *Bremia* resistance trait;
b) screening the segregating population for a member exhibiting resistance to *Bremia*, wherein said trait can be identified by the presence of *Bremia* resistance-conferring introgressed sequence of the invention; and
c) selecting one member of the segregating population, wherein said member comprises the *Bremia* resistance trait.

In another embodiment the invention relates to a method of identifying a lettuce plant comprising the *Bremia* resistance-conferring introgressed sequence of the invention, wherein said method comprises the steps of:

a) providing a population segregating for the *Bremia* resistance trait,
b) screening the segregating population for a member exhibiting resistance to *Bremia*, wherein said trait can be identified by the presence of the *Bremia* resistance-conferring introgressed sequence of the invention, wherein said introgressed sequence of the invention can be identified by detecting (e.g., by genotyping) one or more, two or more, three or more, or all four the *Bremia* resistance associated alleles at markers SL1831, SL1847, SL1883 and/or SL1883 (as described herein); and
c) selecting one member of the segregating population, wherein said member comprises the *Bremia* resistance trait.

In a further embodiment, the invention provides a method for identifying a lettuce plant (e.g., a *L. sativa*, particularly a cultivated *L. sativa*) comprising an introgressed sequence on chromosome 2, wherein said introgressed sequence confers resistance to *Bremia*, the method comprising:

a) providing a population segregating for *Bremia* resistance;
b) screening said population using a kit that detects (e.g., by genotyping):
   i) a G genotype in the heterozygous or homozygous state for SNP marker SL1831 in SEQ ID NO: 1;
   ii) an A genotype in the heterozygous or homozygous state for SNP marker SL1847 in SEQ ID NO: 6;
   iii) a G genotype in the heterozygous or homozygous state for SNP marker SL1887 in SEQ ID NO: 11; and/or
   iv) a C genotype in the heterozygous or homozygous state for SNP marker SL1883 in SEQ ID NO: 16;
c) identifying a plant comprising one or more of the genotypes of (b).

In a further embodiment, the invention provides a method for identifying a wild lettuce source of *Bremia* resistance on chromosome 2, comprising:

a) providing a wild lettuce accession or a plurality of wild lettuce accessions;
b) screening said lettuce accession or plurality of wild lettuce accessions using a kit detects (e.g., by genotyping):
   i) a G genotype in the heterozygous or homozygous state for SNP marker SL1831 in SEQ ID NO: 1;
   ii) an A genotype in the heterozygous or homozygous state for SNP marker SL1847 in SEQ ID NO: 6;
   iii) a G genotype in the heterozygous or homozygous state for SNP marker SL1887 in SEQ ID NO: 11; and/or
   iv) a C genotype in the heterozygous or homozygous state for SNP marker SL1883 in SEQ ID NO: 16; and,
c) identifying a wild lettuce accession comprising one or more of the genotypes of (b).

In yet another embodiment, the invention relates to the use a DNA marker amplified from the genome of a lettuce plant according to any of the preceding embodiments, preferably from the genome of *L. sativa* 18LEN002364, or a progeny or an ancestor thereof, by PCR amplification with the pair of oligonucleotide primers: forward primer of SEQ ID NO: 2 and reverse primer of SEQ ID NO: 5, and probe of SEQ ID NO: 3; forward primer of SEQ ID NO: 7 and reverse primer of SEQ ID NO: 10, and probe of SEQ ID NO: 8; forward primer of SEQ ID NO: 12 and reverse primer of SEQ ID NO: 15, and probe of SEQ ID NO: 13; or forward primer of SEQ ID NO: 17 and reverse primer of SEQ ID NO: 20, and probe of SEQ ID NO: 18, wherein said DNA fragment is indicative of the presence of the *Bremia* resistance trait in a lettuce plant, to identify a lettuce plant that comprises and exhibits the *Bremia* resistance trait.

In embodiments of the methods according to the invention, the method comprises detecting (e.g., by genotyping) the resistance associated genotype (as described herein) at the following SNP markers (each individual marker being present in heterozygous or homozygous form):

SL1831 and SL1847;
SL1831 and SL1883;
SL1831 and SL1887;
SL1847 and SL1883;
SL1847 and SL1887;
SL1883 and SL1887;
SL1831, SL1847 and SL1883;
SL1831, SL1847 and SL1887;
SL1847, SL1883 and SL1887; or
SL1831, SL1847, SL1883 and SL1887.

For example, markers SL1883 and SL1887 can be used together, optionally with the addition of other markers. As another exemplary illustration, markers SL1847 and SL1887 can be used in combination, optionally with the addition of other markers.

Uses.

The present invention also relates to the use of *Bremia* resistance-propagating material obtainable from a lettuce plant according to any of the embodiments of the invention for growing a lettuce plant in order to produce *Bremia* resistant lettuce plants, seeds, heads and/or leaves wherein said *Bremia* resistance may be assessed in a standard assay, particularly an assay as described in Example 1 below.

In embodiments, the invention provides for a method of producing lettuce seed, the method comprising growing a lettuce plant from seed, and allowing the plant to produce further lettuce seed, and optionally collecting the seed.

The present invention also relates to the use of *Bremia* resistance-propagating material obtainable from a lettuce plant according to any of the embodiments of the invention for producing lettuce heads and/or leaves.

The present invention also contemplates the use of the *Bremia* resistance genetic sequences of the present invention in association with other genetic sequences associated with *Bremia* resistance, for instance those genetic sequences discloses in WO2011/003783.

Based on the description of the present invention, the skilled person who is in possession of *L. sativa* 18LEN002364, or a progeny or an ancestor thereof, comprising said introgressed genetic sequence, as described herein, has no difficulty to transfer the said introgressed genetic sequence of the present invention to other lettuce plants of various types using breeding techniques well-known in the art, for example, with the use of SNP marker loci herein disclosed.

Seed Deposit Information

Applicants have made a deposit of at least 2500 seeds of *Lactuca sativa* line 18LEN002364 with the NCIMB (NCIMB Limited, Ferguson Building, Craibstone Estate, Bucksburn, Aberdeen AB21 9YA, Scotland) on 12 Jun. 2020 under NCIMB Accession No. NCIMB 43625.

Applicants elect for the expert solution and request that the deposited material be released only to an Expert according to Rule 32(1) EPC or corresponding laws and rules of other countries or treaties (Expert Witness clause), until the mention of the grant of the patent publishes, or from 20 years from the date of filing if the application is refused, withdrawn or deemed to be withdrawn.

This deposit of *Lactuca sativa* line 18LEN002364 will be maintained in the NCIMB depository, which is a public depository, for a period of 30 years, or 5 years after the most recent request, or for the effective life of the patent, whichever is longer, and will be replaced if any of the deposited seed becomes nonviable during that period. Additionally, Applicants have satisfied all the requirements of 37 C.F.R. §§ 1.801-1.809, including providing an indication of the viability of the samples. Access to this deposit will be made available during the pendency of this application to the Commissioner upon request. Upon the issuance of a patent on the variety, the variety will be irrevocably and without restriction released to the public by providing access to the deposit of at least 2500 seeds of the variety with the NCIMB. Applicants impose no restrictions on the availability of the deposited material from the NCIMB; however, Applicants have no authority to waive any restrictions imposed by law on the transfer of biological material or its transportation in commerce. Applicants do not waive any infringement of its rights granted under this patent or under any plant variety protection rights (e.g., U.S. Plant Variety Protection Act, 7 USC § 2321 et seq.).

The invention will now be described with reference to the following examples. It will be appreciated by those skilled in the art that these examples do not limit the scope of the claims to the invention, but are rather intended to be exemplary of certain embodiments. Other embodiments of the invention may be practiced without departing from the spirit and the scope of the invention, the scope of which is defined by the disclosure and the appended claims.

EXAMPLES

Example 1. Disease Test for *Bremia lactucae*

*Bremia lactucae* disease tests are done in Climate chambers with high humidity. Day length is 16 hours and during the day the temperature is 18° C. and relative humidity (RH) about 85%. During the night the temperature is 15° C. and the RH about 100%. Before inoculation of a test, the spores of the *Bremia* pathogen are multiplied on varieties susceptible to the specific isolate. Disease testing for *Bremia* resistance was performed using various *Bremia* isolates and races.

*Bremia* isolates are characterized and classified according to C-set Sextet code by IBEB (International *Bremia* Evaluation Board; see Table 1).

TABLE 1

Reactions of *Bremia* races BI: 16-36EU to the IBEB C set of differentials

| Race | Sextet code |
|---|---|
| BI: 16 EU | 19-00-00 |
| BI: 17 EU | 45-17-00 |
| BI: 18 EU | 50-00-00 |
| BI: 20 EU | 51-00-00 |
| BI: 21 EU | 27-01-00 |
| BI: 22 EU | 46-32-00 |
| BI: 23 EU | 19-02-00 |
| BI: 24 EU | 50-02-00 |
| BI: 25 EU | 50-01-00 |
| BI: 26 EU | 51-03-00 |
| BI: 27 EU | 47-38-00 |

TABLE 1-continued

Reactions of *Bremia* races BI: 16-36EU to the IBEB C set of differentials

| Race | Sextet code |
|---|---|
| BI: 29 EU | 62-07-00 |
| BI: 30 EU | 46-06-02 |
| BI: 31 EU | 39-12-02 |
| BI: 32 EU | 27-00-04 |
| BI: 33 EU | 62-07-06 |
| BI: 34 EU | 54-15-01 |
| BI: 35 EU | 62-15-06 |
| BI: 36 EU | 55-15-01 |

Before inoculation of test material, the leaves with spores are harvested and the spores rinsed from the leaves with water. The concentration of the spore suspension is adjusted to 100,000 spores per ml. The spore suspension is sprayed over 1-week-old plants (on cotyledons). Seven to 10 days after inoculation the observation/selection can be done. In general, the cotyledons of the susceptible plants are fully covered with spores. Depending on the *Bremia* isolate used, the cotyledons of a resistant plant will show no or low level necrosis with or without sparse sporulation.

Example 2. Breeding History of a *Lactuca sativa* Containing *Bremia* Resistance from a Wild *Lactuca serriola*

The inventors determined that wild *Lactuca serriola* accession CGN23091 has a broad spectrum resistance to *Bremia lactucae*, designated as the "SG01" resistance. A first backcrossing cycle was made to introduce the SG01 *Bremia* resistance from the wild *L. serriola* accession into a susceptible *Lactuca sativa*. This was followed by a backcross into a *L. sativa* Dm0 cultivar, selfing, and a further four rounds of backcrossing, and finally three selfings. The resulting line was designated 18LEN002364 and was deposited with NCIMB on 12 Jun. 2020 under Deposit No. NCIMB 43625. The complete breeding history of the deposited B6F4 breeding line is shown in Table 2 below. This line is fixed for the *Bremia* resistance from the wild *L. serriola* source, i.e., line 18LEN002364 comprises SG01 *Bremia* resistance-conferring introgressed sequences from the wild *L. serriola* accession in the homozygous state.

TABLE 2

Breeding history of a B6F4 *L. sativa* with introgression from *L. serriola* conferring *Bremia lactucae* (downy mildew) resistance

| Generation | (Back) Cross parent | Selection Isolate |
|---|---|---|
| B0 | *L. sativa* Butterhead | |
| B1 | *L. sativa* Butterhead | |
| B2 | *L. sativa* Butterhead | BE736 |
| B3 | *L. sativa* Butterhead (Dm0) | BE736 |
| B3F2 | - (selfing) | FR1021 |
| F2B4 | *L. sativa* Butterhead (Dm0) | FR1021 |
| B5 | *L. sativa* Butterhead (Dm0) | FR1021 |
| B6 | *L. sativa* Butterhead (Dm0) | BI: 29EU |
| B6F2 | - (selfing) | FR1021 |
| B6F3 | - (selfing) | FR1021 |
| B6F4 | - (selfing) → NCIMB Deposit | |

Example 3. Phenotyping *Bremia* Resistance from a Wild *L. serriola* Transferred into *L. sativa*

The *L. sativa* B6F4 line described in Example 2 contains an introgression from wild *L. serriola* accession CGN23091 containing the SG01 *Bremia* resistance locus and has demonstrated resistance against all tested races and isolates of *Bremia lactucae*.

Over a period of at least six years, the SG01 resistance has been tested against approximately 400 field isolates and has provided protection against all isolates evaluated. In addition, the SG01 resistance also protects against all current official European *Bremia* isolates (BI: 16-36EU).

The resistance to the aforementioned *B. lactucae* isolates and races conferred by SG01 is a fast, high level of resistance with no observable necrosis in the plants. Further, the resistance is characterized as dominant (high resistance observed in both heterozygotes and homozygotes), segregation as monogenic, and qualitative in nature.

Example 4. The SG01 *Bremia* Resistance is Fixed and Protects in Other Genetic Backgrounds The SG01 *Bremia* resistance from *L. serriola* accession CGN23091 has been fixed from the BC6 and later generations shown in Table 1 above. The SG01 resistance has been successfully transferred into other *L. sativa* genetic backgrounds. The deposited line was further backcrossed into a commercial butterhead variety, followed by a final two selfings. An advanced backcross line was used as a source to introduce the *Bremia* resistance into multiple lettuce segments (including baby leaf, multi leaf, romaine, iceberg, and indoor and outdoor butterhead). At each step of the breeding process, plants selected for the next generation were tested (by genotyping and phenotyping) and the presence of the resistance was confirmed against a panel of *Bremia* isolates. The fast and high level qualitative *Bremia* resistance was maintained against the subset of isolates tested and in all genetic backgrounds and under all environmental conditions evaluated. These results confirm the heritable genetic basis of the SG01 resistance.

Example 5. Mapping and Genotyping the SG01 *Bremia* Resistance Locus from *L. serriola*

The SG01 *Bremia* resistance introgression from *L. serriola* has been backcrossed into a *L. sativa* Dm0 cultivar up to the B6 generation (Table 1 above). This B6 line has been shown to have *Bremia* resistance under field conditions (Example 2), with an absence of linkage drag.

Material and Methods

A: Assay Development

Step 1: Microarray Development

An array was developed composed of 2500 SNPs spread over the *L. sativa* genome. The variants were identified by comparing sequences obtained by reduced-sequencing of a panel of 17 *L. sativa* varieties/accessions across different segments (including batavia, butterhead, cos, iceberg and multileaf).

The array was used to fingerprint backcross (BC) lines and the recurrent parent deriving from the *Bremia* program.

Step 2: Fingerprinting: Identification of the Introgression

The fingerprinting screen indicated the BC lines (CGN23091: B7F2) are 96-98% identical to the recurrent parent. The SG01 *Bremia* resistance was associated with an introgression region found in BC lines deriving from CGN23091.

A first estimation of the introgression size was 33 MB on linkage group 2 from position 4119137 to 37019114 bp using the reference *Lactuca sativa* v5 physical map (Reyes- Chin-Wo et al., (2017) Nat. Commun. 8, 14953). This region co-locates with the major resistance gene cluster harboring Dm3, but SG01 is a distinct locus from Dm3 and has a different resistance spectrum.

Step 3: Development of Chromosome 2 SG01 *Bremia* Resistance Specific Markers

Using Next-Generation sequencing (Mardis, (2008) Annual Review of Genomics and Human Genetics 9: 387), whole genome DNA sequencing (WGS) or reduced genome sequencing (RGS) was performed on the recurrent Dm0 parent and a panel of commercial varieties and wild *L. serriola* accessions harboring a *Bremia* resistance introgression on chromosome 2.

Alignment with the reference *Lactuca sativa* v5 sequence and the recurrent susceptible Dm0 parent identified 147,465 variants between 4119137 nt to 10787672 nt on linkage group 2 (LG2). Furthermore, 94,376 variants reflected the different allelic states between the susceptible Dm0 recurrent parent and the resistant backcross line within the introgression region of interest.

Step 4: Mapping and Fine-Mapping

Variants from Step 3 with different allelic states between the resistant backcross line and susceptible DMO recurrent parent across the SG01 introgression were selected and converted into Taqman™ PCR assays to detect SNPs. Complementary to phenotyping for *Bremia* resistance, the markers were used to test a large CGN23091 B7F4 population (295 individuals) from the recurrent Dm0 parent. From the 37 putative SNP candidates, two SNPs, SL1847 and SL1831, showed 100% co-segregation with *Bremia* resistance, as calculated by JoinMap® (Table 3). SNP markers SL1883 and SL1887 were also closely linked to the resistance. The specificity of the markers can be increased further by using a haplotype composed of 2 or more markers from Table 3, for example, within approximately 1 cM distance from the resistance locus (e.g., any two or any three of markers SL1887, SL1883, SL1847 and SL1831, or all four of these markers).

These markers can be used singly, or in any combination, to identify lettuce plants comprising the SG01 *Bremia* resistance, to follow the resistance for introgression into new lines, and the like. For example, markers SL1883 and SL1887 can be used together, optionally with the addition of other markers. As another exemplary illustration, markers SL1847 and SL1887 can be used in combination, optionally with the addition of other markers.

TABLE 3

| Genetic map | | | | |
|---|---|---|---|---|
| Locus | Position (cM) | LOG10(P) | Count | Physical position on V5 |
| SL1788 | 0 | 0.208 | 271 | 9488082 |
| SL1812 | 2.131 | 0.203 | 270 | 9488424 |
| SL1785 | 2.582 | 0.198 | 267 | 9488098 |
| SL1794 | 3.543 | 0.194 | 269 | 9488150 |
| SL1787 | 7.885 | 0.029 | 145 | 9488433 |
| SL1889 | 8.496 | 0.078 | 295 | 10785280 |
| SL1826 | 16.408 | 0.156 | 252 | 10423317 |
| SL1883 | 17.715 | 0.044 | 294 | 8857532 |
| SL1887 | 17.949 | 0.008 | 295 | 9514234 |
| Resistance | 17.957 | 0 | 295 | |
| SL1847 | 17.957 | 0 | 295 | 8863685 |
| SL1831 | 17.957 | 0 | 295 | 9490681 |
| SL1842 | 18.180 | 0 | 295 | 7841320 |
| SL1875 | 18.180 | 0 | 295 | 8247082 |
| SL1872 | 18.180 | 0 | 295 | 7788015 |
| SL1892 | 18.180 | 0 | 295 | 10343301 |
| SL1843 | 18.221 | 0 | 294 | 7835585 |

TABLE 3-continued

| Genetic map | | | | |
|---|---|---|---|---|
| Locus | Position (cM) | LOG10(P) | Count | Physical position on V5 |
| SL1839 | 18.238 | 0 | 295 | 10484774 |
| SL1884 | 18.241 | 0 | 294 | 7893169 |
| SL1858 | 18.270 | 0.02 | 289 | 10386355 |
| SL1821 | 18.542 | 0.02 | 295 | 6630356 |
| SL1853 | 18.583 | 0 | 295 | 6615901 |
| SL1873 | 18.583 | 0 | 295 | 6742850 |
| SL1844 | 18.583 | 0 | 295 | 4216946 |
| SL1810 | 18.583 | 0 | 295 | 6630579 |
| SL1840 | 18.673 | 0 | 295 | 5884770 |
| SL1845 | 18.673 | 0 | 295 | 4304911 |
| SL1870 | 18.673 | 0 | 295 | 5052021 |
| SL1893 | 18.700 | 0.022 | 295 | 5460857 |
| SL1816 | 18.776 | 0.033 | 285 | 6630356 |
| SL1837 | 28.054 | 0.013 | 294 | 10417767 |
| SL1857 | 28.119 | 0.01 | 295 | 6630824 |
| SL1914 | 28.297 | 0.023 | 295 | 5463246 |
| SL1834 | 56.193 | 0.073 | 289 | 4209705 |
| SL1916 | 57.590 | 0.074 | 294 | 5905052 |

The physical positions of SNP markers SL1831, SL1847, SL1883 and SL1887, and PCR primers/probes for detection these SNPs are shown below:

SNP SL1831 at 9 490 680 bp on LG2 (based on reference *L. sativa* v5 sequence)
Target Sequence:

(SEQ ID NO: 1)
TNTAAAGATTAGATACAGGGCAGGGAGGAATGCCTTTGAGATAAATGAGG

NGATCGACAGTGTCATGAGACGATACAAAGAGATCAACCNGGCAGATCAT

NCAATTCCTCC[A/G]GGAAGGGTTGATTCCATGAAGCCATCCACATCAA

CACCATCAG

>RESISTANCE ALLELE: G
>PRIMER FORWARD (underline)

(SEQ ID NO: 2)
AGATACAGGGCAGGGAGGAATG

>PROBE (double underline)
Detect resistant allele:

(SEQ ID NO: 3)
ACCCTTCCCGGAGGA

Detect susceptible allele:

(SEQ ID NO: 4)
CAACCCTTCCTGGAGG

>PRIMER REVERSE (underline)

(SEQ ID NO: 5)
TGATGTGGATGGCTTCATGGAAT

SNP SL1847 at 8 893 684 bp on LG2 (based on reference *L. sativa* v5 sequence)
Target Sequence:

(SEQ ID NO: 6)
GGTACACGCTCGCAGTGAAAGCCTTGGAGATAACTCAGGAGATCGATCAT

GCCATGAAACAACTCTCTCAGATAGAATGGACTGATGATTCAGTTCCTTT

NGGNAGAAATG[G/A]TTCCACAAAGGCATCCACCTCTACACCATCAAGT

GATTACAATGA

>RESISTANCE ALLELE: A
>PRIMER FORWARD (underline)

(SEQ ID NO: 7)
CGCAGTGAAAGCCTTGGAGAT

-continued

>PROBE (double underline)
Detect the resistant allele:

(SEQ ID NO: 8)
TGCCTTTGTGGAATCATTT

Detect the susceptible allele:

(SEQ ID NO: 9)
CCTTTGTGGAACCATTTC

>PRIMER REVERSE (underline)

(SEQ ID NO: 10)
CACTTGATGGTGTAGAGGTGGA

SL1887 at 9 514 233 bp on LG2 (based on reference *L. sativa* v5 sequence)
Target Sequence (SEQ ID NO: 11)
GCACTTGCAAGCATGAGACAGCTCGAAGAGTTAACTATAAATATATTGCAA

GGCCTTGAAAGNGATTGTGAAGAAGGAAGAAGACAATGCATCATCATC

[A/G]TCATCGAAGGAGGTTGTGGTCTTGCCTCATCTAAAGTCC

>RESISTANCE ALLELE: G
>PRIMER FORWARD (underline)

(SEQ ID NO: 12)
GCATGAGACAGCTCGAAGAGT

>PROBE (double underline)
Detect the resistant allele:

(SEQ ID NO: 13)
CCTTCGATGACGATGATG

Detect the susceptible allele:

(SEQ ID NO: 14)
TCCTTCGATGATGATGATG

>PRIMER REVERSE (underline)

(SEQ ID NO: 15)
TGAGGCAAGACCACAACC

-continued

SL1883 at 8 857 531 bp on LG2 (based on reference *L. sativa* v5 sequence)
Target Sequence (SEQ ID NO: 16)
AGACGNTTTAACGACCTGGCCCAACATTCCATGAACCACC[A/C]GACTG

GTTTTGGGCAATTTAGTCGGGTACCTGCCTTTGC

>RESISTANCE ALLELE: C
>PRIMER FORWARD (underline)

(SEQ ID NO: 17)
ACGACCTGGCCCAACATTCC

>PROBE (double underline)
Detect the resistant allele):

(SEQ ID NO: 18)
TGAACCACCCGACTG

Detect the susceptible allele:

(SEQ ID NO: 19)
TGAACCACCAGACTGG

>PRIMER REVERSE (underline)

(SEQ ID NO: 20)
GTACCCGACTAAATTGCCCAAA

The information above is summarized in Table 4 below:

TABLE 4

| MARKER | SL1831 | SL1847 | SL1887 | SL1883 |
|---|---|---|---|---|
| Resistance Allele[1] | G | A | G | C |
| Susceptible Allele | A | G | A | A |
| Target Sequence: SEQ ID NO. | 1 | 6 | 11 | 16 |
| SNP Position in Target: nt | 112 | 112 | 99 | 41 |
| Forward Primer: SEQ ID NO. | 2 | 7 | 12 | 17 |
| Reverse Primer: SEQ ID NO. | 5 | 10 | 15 | 20 |
| Probe (Resistant): SEQ ID NO. | 3 | 8 | 13 | 18 |
| Probe (Susceptible): SEQ ID NO. | 4 | 9 | 14 | 19 |

[1]Resistance present in both heterozygotes and homozygotes

Although the present invention has been described with reference to specific details of certain embodiments thereof, it is not intended that such details should be regarded as limitations upon the scope of the claimed invention except as and to the extent that they are included in the accompanying claims.

That which is claimed is:

1. A method for producing a lettuce plant with enhanced resistance to *Bremia lactucae*, the method comprising:

a) crossing a *Lactuca sativa* plant with a lettuce plant to produce progeny plants, wherein:

i) the *Lactuca sativa* plant has enhanced resistance to *Bremia lactucae* and comprises an introgressed sequence from *Lactuca serriola* that confers a qualitative and dominant resistance to *Bremia lactucae*, wherein said introgressed sequence is comprised in *Lactuca sativa* line 18LEN002364, representative seed of *L. sativa* 18LEN002364 having been deposited with the NCIMB under Accession No. NCIMB 43625, wherein the resistance of the plant to *Bremia lactucae* is enhanced as compared with a *L. sativa* plant lacking said introgressed sequence, and wherein said introgressed sequence is located on chromosome 2 and comprises one or more of the following SNP markers:

a) a G genotype in the heterozygous or homozygous state for SNP marker SL1831 in SEQ ID NO: 1;

b) an A genotype in the heterozygous or homozygous state for SNP marker SL1847 in SEQ ID NO: 6;

c) a G genotype in the heterozygous or homozygous state for SNP marker SL1887 in SEQ ID NO: 11; and/or d) a C genotype in the heterozygous or homozygous state for SNP marker SL1883 in SEQ ID NO: 16; and ii) the lettuce plant lacks said introgressed sequence conferring resistance to *Bremia lactucae*; and b) selecting a progeny plant comprising said introgressed sequence conferring resistance to *Bremia lactucae*, said selecting step comprising detecting one or more of the following SNP markers:

i) a G genotype in the heterozygous or homozygous state for SNP marker SL1831 in SEQ ID NO: 1;

ii) an A genotype in the heterozygous or homozygous state for SNP marker SL1847 in SEQ ID NO: 6;

iii) a G genotype in the heterozygous or homozygous state for SNP marker SL1887 in SEQ ID NO: 11; and/or iv) a C genotype in the heterozygous or homozygous state for SNP marker SL1883 in SEQ ID NO: 16;

thereby producing a plant with enhanced resistance to *Bremia lactucae*.

2. The method according to claim 1, wherein the method further comprises:

c) selfing the selected progeny or crossing the selected progeny with another lettuce plant to produce further progeny.

3. The method according to claim 2, wherein further progeny are selected and selfed and/or crossed for 2 to 10 more generations.

4. The method according to claim 1, wherein said selecting step of b) comprises detecting two or more of said SNP markers SL1831, SL1847, SL1887 and/or SL1883.

5. The method according to claim 4, wherein said selecting step comprises detecting at least the following SNP markers:

SL1831 and SL1847;
SL1831 and SL1883;
SL1831 and SL1887;
SL1847 and SL1883;
SL1847 and SL1887; or
SL1883 and SL1887.

6. A method for producing a F1 hybrid lettuce plant with enhanced resistance to *Bremia lactucae*, the method comprising crossing a first inbred *Lactuca sativa* plant with a different inbred *L. sativa* plant to produce F1 hybrid progeny, wherein:

i) the first inbred *L. sativa* plant has enhanced resistance to *Bremia lactucae* and comprises an introgressed sequence from *Lactuca serriola* that confers a qualitative and dominant resistance to *Bremia lactucae*, wherein said introgressed sequence is comprised in *Lactuca sativa* line 18LEN002364, representative seed of *L. sativa* 18LEN002364 having been deposited with the NCIMB under Accession No. NCIMB 43625, wherein the resistance of the plant to *Bremia lactucae* is enhanced as compared with a *L. sativa* plant lacking said introgressed sequence, and wherein said introgressed sequence is located on chromosome 2 and comprises one or more of the following SNP markers:
a) a G genotype in the heterozygous or homozygous state for SNP marker SL1831 in SEQ ID NO: 1;
b) an A genotype in the heterozygous or homozygous state for SNP marker SL1847 in SEQ ID NO: 6;
c) a G genotype in the heterozygous or homozygous state for SNP marker SL1887 in SEQ ID NO: 11; and/or
d) a C genotype in the heterozygous or homozygous state for SNP marker SL1883 in SEQ ID NO: 16.

7. A method for identifying a lettuce plant with enhanced resistance to *Bremia lactucae*, said method comprising the step of detecting one or more of the following SNP markers:
a) a G genotype in the heterozygous or homozygous state for SNP marker SL1831 in SEQ ID NO: 1;
b) an A genotype in the heterozygous or homozygous state for SNP marker SL1847 in SEQ ID NO: 6;
c) a G genotype in the heterozygous or homozygous state for SNP marker SL1887 in SEQ ID NO: 11; and/or
d) a C genotype in the heterozygous or homozygous state for SNP marker SL1883 in SEQ ID NO: 16;

thereby identifying a lettuce plant with enhanced resistance to *Bremia lactucae*.

8. The method according to claim 7, wherein said method further comprises selecting a lettuce plant comprising said one or more SNP markers, and crossing the selected lettuce plant with a second lettuce plant to produce progeny lettuce plants that comprise the one or more molecular markers and have enhanced resistance to *Bremia lactucae*.

9. The method according to claim 7, wherein said detecting step comprises detecting two or more of said SNP markers SL1831, SL1847, SL1887 and/or SL1883.

10. The method according to claim 9, wherein said detecting step comprises detecting at least the following SNP markers:
SL1831 and SL1847;
SL1831 and SL1883;
SL1831 and SL1887;
SL1847 and SL1883;
SL1847 and SL1887; or
SL1883 and SL1887.

11. A method of producing lettuce seed, the method comprising growing a lettuce plant from a seed, and allowing the plant to produce further lettuce seed, wherein:

i) the seed produces a *Lactuca sativa* plant that has enhanced resistance to *Bremia lactucae* and comprises an introgressed sequence from *Lactuca serriola* that confers a qualitative and dominant resistance to *Bremia lactucae*, wherein said introgressed sequence is comprised in *Lactuca sativa* line 18LEN002364, representative seed of *L. sativa* 18LEN002364 having been deposited with the NCIMB under Accession No. NCIMB 43625, wherein the resistance of the plant to *Bremia lactucae* is enhanced as compared with a *L. sativa* plant lacking said introgressed sequence, and wherein said introgressed sequence is located on chromosome 2 and comprises one or more of the following SNP markers:
a) a G genotype in the heterozygous or homozygous state for SNP marker SL1831 in SEQ ID NO: 1;
b) an A genotype in the heterozygous or homozygous state for SNP marker SL1847 in SEQ ID NO: 6;
c) a G genotype in the heterozygous or homozygous state for SNP marker SL1887 in SEQ ID NO: 11; and/or
d) a C genotype in the heterozygous or homozygous state for SNP marker SL1883 in SEQ ID NO: 16.

* * * * *